United States Patent [19]

Jørgensen et al.

[11] Patent Number: 5,681,715
[45] Date of Patent: Oct. 28, 1997

[54] PROCESS FOR PREPARING LIPASES

[75] Inventors: Steen Troels Jørgensen, Alleroed; Boerge Krag Diderichsen, Birkeroed, both of Denmark; Catherine M. Buckley, Cork, Ireland; Audrey Hobson, Go. Wicklow, Ireland; David J. McConnell, Co. Dublin, Ireland

[73] Assignee: Novo Nordisk A/S, Bagsvaerd, Denmark

[21] Appl. No.: 400,422

[22] Filed: Mar. 3, 1995

Related U.S. Application Data

[63] Continuation of Ser. No. 38,763, filed as PCT/DK92/00391, Dec. 18, 1992, abandoned.

[30] Foreign Application Priority Data

Dec. 20, 1991 [WO] WIPO ............... PCT/DK91/00402

[51] Int. Cl.$^6$ ............... C12N 15/52; C12N 15/31; C12N 9/20
[52] U.S. Cl. ............... 435/69.1; 435/69.7; 435/198; 435/252.3; 435/252.33; 435/320.1; 435/325; 536/23.2; 536/23.4; 536/23.7
[58] Field of Search ............... 435/69.1, 198, 435/252.3, 252.33, 320.1, 874, 69.7, 7, 325; 530/412; 536/23.2, 23.4, 23.7

[56] References Cited

FOREIGN PATENT DOCUMENTS 0 464 922   1/1992   European Pat. Off. .
WO 91/00908 1/1991   WIPO .

OTHER PUBLICATIONS

Hager et al "Elustion of Proteins . . . " Analy. Biochemistry 109:76–86 1980.
Jorgensen et al. "Cloning, Sequencing . . . " J. Bact. 173:559–567 Jan. 1991.

Primary Examiner—Keith C. Furman
Attorney, Agent, or Firm—Steve T. Zelson, Esq.; Valeta Gregg, Esq.

[57] ABSTRACT

A process for producing an active lipase enzyme in vitro, comprising mixing an inactive or partly active lipase enzyme with a chaperone molecule and subjecting the mixture to denaturation followed by renaturation to produce the active lipase enzyme.

39 Claims, 13 Drawing Sheets

PROCESS FOR PREPARING LIPASES

This application is a continuation of application Ser. No. 08/038,763, now abandoned, filed as PCT/DK92/00391, Dec. 18, 1992, the contents of which are incorporated herein by reference.

FIELD OF INVENTION

The present invention relates to processes for preparing an active lipase enzyme in vitro, a DNA construct encoding the lipase, a recombinant vector including the DNA construct, as well as a host cell transformed with the vector.

BACKGROUND OF THE INVENTION

Lipases are enzymes which catalyze the hydrolysis of ester bonds in triglycerides resulting in the formation of diglycerides, monoglycerides, glycerin and free fatty acids. Some lipases also catalyze other reactions involving ester bonds such as synthesis of ester bonds or transesterification reactions. Lipases are produced by a wide variety of different organisms. Microbial lipases in particular are of considerable practical utility for a variety of purposes where lipolysis of fats is desired, e.g. in the food industry and in detergents.

One particular lipase which has been found to be particularly advantageous for inclusion in a detergent for the removal of fatty stains or soiling from fabrics is a lipase produced by strains of *Pseudomonas cepacia*. In EP 214 761 (to Novo Industri A/S), this lipase is disclosed as a lipase which is active at a temperature below 60° C., which is important as most present-day fabrics are washed at temperatures below 60° C.

Another important *Pseudomonas cepacia* lipase for use as a detergent additive is the one disclosed in WO 89/01032 (to Novo Industri A/S) as a positionally non-specific lipase, i.e. one which is able to react with all three fatty acyl groups of a triglyceride.

In order to facilitate *Pseudomonas cepacia* lipase production, it may be advantageous to employ recombinant DNA techniques, for instance in order to optimize lipase expression by introducing a stronger promoter from which the DNA sequence encoding the enzyme is expressed or by introducing more efficient ribosome binding sites or signal peptide coding sequences, or in order to select a host organism for the production of the enzyme which is easier to cultivate (e.g. in terms of its being a standard production organism such as *E. coli* or the like) or which results in higher lipase yields.

However, as described below, such approaches will sometimes fail to yield the expected results, e.g. in cases where one or more genes in addition to the structural gene coding for the protein in question, play some part in the production of the gene product (examples of such genes are the Bacillus sac and iep genes, and genes required for the production of *Klebsiella pullulanase* and *E. coli* hemolysin).

The cloning of a lipase gene from another Pseudomonas species, *Pseudomonas fragi*, is known from, e.g., S. Aoyama et al., FEBS Letters, Vol. 242, No. 1, pp. 36–40 (1988) and Kugimiya et al., Biochem. Biophys. Res. Comm., Vol. 141, No. 1, pp. 185–90 (1986). However, the lipase produced by *P.fragi* differs from that of *P. cepacia* in its amino acid sequence, and in these publications, there is no indication that one or more additional genes may be required in order to achieve a significant lipase production in a host organism.

EP 331 376 discloses a recombinant DNA encoding a *Pseudomonas cepacia* lipase as well as a protein participating in the production of the lipase.

WO 90/00908 discloses the production of a *Pseudomonas cepacia* lipase in heterologous host cells by means of a polypeptide expressed in the host cell, which polypeptide acts as a modulator of lipase production.

SUMMARY OF THE INVENTION

It has surprisingly been found possible to increase the yield of an active lipase enzyme produced by a recombinant host cell when the lipase recovered from the cells is subjected to denaturation followed by renaturation in the presence of a chaperone molecule.

Accordingly, the present invention relates to a process for preparing an active lipase enzyme in vitro, the process comprising (a) culturing a host cell transformed with a DNA sequence encoding a lipase enzyme under suitable conditions to produce the lipase enzyme in inactive or partly active form, recovering the lipase enzyme from the culture, and subjecting the recovered lipase enzyme to denaturation, (b) mixing the denaturated lipase enzyme with a chaperone molecule, and (c) subjecting the mixture of step (b) to renaturation to produce the active lipase enzyme.

Alternatively, the invention relates to a process for preparing an active lipase enzyme in vitro, the process comprising (a) culturing a host cell transformed with a DNA sequence encoding a lipase enzyme under suitable conditions to produce the lipase enzyme in inactive or partly active form and recovering the lipase enzyme from the culture, (b) mixing the recovered lipase enzyme with a chaperone molecule, and (c) subjecting the mixture of step (b) to denaturation followed by renaturation to produce the active lipase enzyme.

In a further embodiment, the invention relates to a process for preparing an active lipase enzyme in vitro, the process comprising (a) culturing a host cell transformed with a DNA sequence encoding a lipase enzyme and with a DNA sequence encoding a chaperone molecule under suitable conditions to produce the lipase enzyme in inactive or partly active form and recovering a lipase enzyme chaperone molecule mixture from the culture, and (b) subjecting the mixture of step (a) to denaturation followed by renaturation to produce the active lipase enzyme, optionally with addition of a further amount of chaperone molecule to the mixture.

As indicated above, the present invention is based on the finding that the natural conformation of a protein or protein complex is not always only determined by the amino acid sequence of the protein. Thus, in some cases, accessory proteins, termed chaperone molecules, are required to mediate the formation of the correct tertiary structure of another protein or protein complex, but are not themselves components of the final functional structure (Ellis et al., Annual Review of Biochemistry, Vol. 60, pp. 321–47 (1991)).

In the present context, the term "chaperone molecule" is intended to indicate such accessory proteins, i.e. a protein involved in facilitating other polypeptides in maintaining the unfolded state, enabling their correct transmembrane targeting or folding and oligomeric assembly, and in disassembly of protein complexes (cf. Ellis et al., Trends Biochem. Sci., Vol. 14, pp. 339–42 (1989), Rothman, Cell, Vol. 59, pp. 591–601 (1989) and Morimoto et al., *Stress Proteins in Biology and Medicine*, Cold Spring Harbor Laboratory, Cold Spring Harbor, N.Y., pp. 1–36 (1990)). Although, in general, a covalent modification of the target protein or protein complex has not been observed by the action of a chaperone molecule it cannot be excluded that the chaperone molecule to be used in the processes of the invention is capable of causing such covalent modification. Accordingly, the term "chaperone molecule" as used herein is intended to include a chaperone molecule causing non-covalent as well as covalent modification of the lipase enzyme.

In another aspect, the present invention relates to a DNA construct comprising a first DNA sequence encoding a lipase enzyme fused to a second DNA sequence encoding a chaperone molecule in such a way that the lipase enzyme and chaperone molecule or functional part thereof are expressed as a single fusion protein on culturing a suitable host cell transformed with the DNA construct.

DETAILED DISCLOSURE OF THE INVENTION

The chaperone molecule to be added to the recovered and optionally denaturated lipase enzyme in step b) above is advantageously produced by a process comprising culturing a host cell transformed with a DNA sequence encoding a chaperone molecule under suitable conditions to produce the chaperone molecule and recovering the chaperone molecule from the culture. Furthermore, when the chaperone molecule is to be added to a denaturated lipase enzyme it may be advantageous that the chaperone molecule itself is denaturated. Accordingly, the process of the invention may comprise a further step in which the chaperone molecule is subjected to a denaturation treatment before it is mixed with the denatured lipase enzyme in step b).

In the present context, "partly active form" as used about the lipase enzyme is intended to indicate that the lipase has some, but not full activity as determined by an activity measurement, e.g. by titration using a pH stat as later described. Less than full activity is taken to mean, that the partly active lipase preparation has a lower specific activity than a corresponding preparation of fully active lipase protein, the two preparations containing the same total amount of lipase protein.

The denaturation of the inactive or partly active lipase enzyme and optionally the chaperone molecule, which may be performed separately or on a mixture of the two components according to the processes of the invention may be carried out in a manner known per se. For instance, the denaturation may be obtained by subjecting the mixture to the action of a denaturating agent (e.g. 8M urea) and subsequently removing this agent, e.g. by dialysis.

Preferred lipases for production by the process of the invention are lipases derived from a Pseudomonas sp. or a Chromobacter sp. In particular, the lipase enzyme may be a *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae* (e.g. as described in EP 407 225), *Pseudomonas aeruginosa* or *Chromobacter viscosum* lipase, or a derivative of said lipase enzyme. In particular, the lipase enzyme is one derived from a strain of *Pseudomonas cepacia*, e.g. a strain deposited in the Deutsche Sammlung von Mikroorganismen in connection with the invention disclosed in EP 214 761, with the deposit numbers DSM 3333–3337 and DSM 3401, as well as the strain deposited in the Deutsche Sammlung von Mikroorganismen in connection with the invention disclosed in WO 89/01032, with the deposit number DSM 3959.

In the present context, the term "derivative" is intended to indicate a protein with lipolytic activity which is derived from the native lipase by suitably modifying the DNA sequence coding for the native lipase, resulting in the addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence. Such modifications of DNA coding for native proteins are well known and widely practiced in the art. Typically, the amino acid sequence of the derivative will be homologous to that of the native lipase protein, e.g. exhibiting a substantial degree of homology, or the derivative will react with an antibody raised against the native lipase.

The host cell used in the process of the invention may be any suitable bacterium which, on cultivation, produces large amounts of the lipase. Examples of suitable bacteria may be grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus* or *Streptomyces lividans*. It has been found that *E. coli* is able to produce a high yield, i.e. at least 5% of the total cellular protein, of (intracellular) lipase, and is therefore a preferred host organism. In *E. coli*, the lipase enzyme is typically produced in the form of inclusion bodies. The transformation of the bacteria may for instance be effected by protoplast transformation or by using competent cells in a manner known per se. Another suitable bacterial host cell is a cell of a Pseudomonas spp. such as *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae* or *Pseudomonas aeruginosa*.

Alternatively, the host cell may be a fungus, i.e. a cell of a yeast or of a filamentous fungus. The yeast host cell may, for instance, be a cell of the genus Saccharomyces such as *S. cerevisiae*. The filamentous fungus host organism may conveniently be one which has previously been used as a host for producing recombinant proteins, e.g. a strain of Aspergillus sp., such as *A. niger, A. nidulans* or *A. oryzae*. The techniques used to transform a fungal host cell and obtain expression of the recombinant protein may suitably be as described in EP 238 023.

For expression of the protein in the host cell the DNA sequence encoding the protein may be preceded by a promoter. The promoter may be any DNA sequence exhibiting a strong transcriptional activity in the host cell of choice and may be derived from a gene encoding an extracellular or intracellular protein such as an amylase, a glucoamylase, a protease, a lipase, a cellulase or a glycolytic enzyme.

Other sequences involved in expression of the protein include termination and polyadenylation sequences as well as ribosome binding sites and may suitably be derived from the same sources as the promoter.

In the process of the invention, the DNA sequence encoding the lipase enzyme and/or the chaperone molecule is advantageously preceded by the promoter of the *Bacillus*

*stearothermophilus* maltogenic amylase gene, *Bacillus licheniformis* α-amylase gene, *Bacillus amyloliquefaciens* α-amylase gene, *Bacillus subtilis* alkaline protease gene, or *Bacillus pumilus* xylosidase gene, or by the phage Lambda $P_R$ or $P_L$ promoters, the phage T7 gene 10 promoter or the *E. coli* lac promoter. The DNA sequence encoding the lipase enzyme and/or the chaperone molecule may be preceded by a ribosome binding site of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, *Bacillus pumilus* xylosidase gene, phage T7 gene 10 or *E. coli* lac gene.

According to the invention, the chaperone molecule is advantageously a Pseudomonas lipase modulator protein, preferably selected from the group consisting of the *Pseudomonas cepacia* lipase modulator (disclosed in WO 90/00908), the *Pseudomonas glumae* lipase modulator, and the *Pseudomonas aeroginosa* lipase modulator, or a derivative of any such lipase modulator.

In the present context, a derivative of a lipase modulator is to be understood in the same manner as indicated above in connection with derivatives of the lipase enzyme, i.e. a protein with chaperone activity which is derived from the native lipase by suitably modifying the DNA sequence coding for the native lipase modulator as discussed above. The chaperone activity of the derivative may, for instance, be determined by analyzing the capability of the derivative in producing an active lipase enzyme as explained herein.

In a preferred embodiment of the process according to the invention, the lipase enzyme is a *Pseudomonas cepacia* lipase or a derivative thereof, and the chaperone molecule is a *Pseudomonas cepacia* lipase modulator (or a derivative thereof) (both disclosed in WO 90/00908).

The DNA construct of the invention comprising the DNA sequence encoding the lipase enzyme and/or the chaperone molecule may be of genomic or cDNA origin, for instance obtained by preparing a genomic or cDNA library of an appropriate organism, and screening for DNA sequences coding for all or part of the lipase or the chaperone by hybridization using synthetic oligonucleotide probes in accordance with standard techniques (cf. Sambrook et al., *Molecular Cloning: A Laboratory Manual*, Cold Spring Harbor (1989)).

The DNA construct of the invention may also be prepared synthetically by established standard methods, e.g. the phosphoamidite method described by Beaucage et al., Tetrahedron Letters, Vol. 22, pp. 1859–69 (1981) and Matthes et al., EMBO Journal, Vol. 3, pp. 801–05 (1984). According to the phosphoamidite method, oligonucleotides are synthesized, e.g. in an automatic DNA synthesizer, purified, ligated, and cloned in an appropriate vector.

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques.

In the DNA construct of the invention, the DNA sequence encoding the lipase enzyme may be one derived from a Pseudomonas sp. or a Chromobacter sp. For instance, the first DNA sequence may be one encoding a *Pseudomonas cepacia*, *Pseudomonas fragi*, *Pseudomonas gladioli*, *Pseudomonas fluorescens*, *Pseudomonas stutzeri*, *Pseudomonas alcaligenes*, *Pseudomonas pseudoalcaligenes*, *Pseudomonas putida*, *Pseudomonas glumae*, *Pseudomonas aeruginosa* or *Chromobacter viscosum* lipase, or a derivative of said lipase enzyme. The second DNA sequence may be one encoding a *Pseudomonas cepacia* lipase modulator, a *Pseudomonas glumae* lipase modulator, a *Pseudomonas aeroginosa* lipase modulator, or another Pseudomonas lipase modulator protein or a derivative of any of these modulators. Most preferably, the first DNA sequence encodes a *Pseudomonas cepacia* lipase or a derivative thereof, and the second DNA sequence encodes a *Pseudomonas cepacia* lipase modulator or a derivative thereof, as described in WO 90/00908 incorporated herein by reference.

A particularly preferred DNA construct is one which has the sequence shown in SEQ ID NO:5 appended hereto. The sequence may be modified in accordance with conventional practice. Examples of suitable modifications of the DNA sequence are nucleotide substitutions which do not give rise to another amino acid sequence of the lipase or lipase modulator, but which may correspond to the codon usage of the host organism into which the DNA construct is introduced or nucleotide substitutions which do give rise to a different amino acid sequence and therefore, possibly, a different polypeptide structure without, however, impairing the properties of either the lipase or the lipase modulator. Other examples of possible modifications are insertion of one or more nucleotides into the sequence, addition of one or more nucleotides at either end of the sequence and deletion of one or more nucleotides at either end of or within the sequence.

In a further aspect, the invention relates to a recombinant expression vector comprising a DNA construct as described above. The expression vector carrying the DNA sequence encoding the lipase and/or chaperone molecule may be any vector which is capable of replicating autonomously in a given host organism, typically a plasmid or bacteriophage. In the vector, the DNA sequence encoding the lipase and/or chaperone molecule should be operably connected to a suitable promoter sequence. The promoter may be any DNA sequence which shows transcriptional activity in the host cell and may be derived from genes encoding proteins either homologous or heterologous to the host organism. The promoter is preferably the promoter of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, or *Bacillus pumilus* xylosidase gene, or by the phage Lambda $P_R$ or $P_L$ promoters, the phage T7 gene 10 promoter or the *E. coli* lac promoter.

The vector may also comprise a selectable marker, e.g. a gene whose product confers antibiotic resistance, such as ampicillin, chloramphenicol or tetracycline resistance, or the dal genes from *B.subtilis* or *B.licheniformis*.

In a still further aspect, the present invention relates to a process for preparing a lipase in active form, the process comprising culturing a host cell transformed with the DNA construct described above under suitable conditions to produce the lipase, and recovering the lipase from the culture, optionally followed by denaturation and renaturation of the lipase/chaperone fusion protein.

The medium used to cultivate the cells may be any conventional medium suitable for growing bacteria. The lipase may be recovered from the medium by conventional procedures including separating the cells from the medium by centrifugation or filtration, if necessary after disruption of the cells to recover an intracellular product, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

While the use of chaperone molecules in the preparation of active lipase enzyme is considered to be of particular importance in connection with recombinant DNA techniques (as explained above), it is believed that the presence of a chaperone molecule is critical in connection with any denaturation and renaturation treatment in which an active lipase enzyme, as described herein, is desired, irrespectively of the production method of the lipase enzyme. Thus, for instance in connection with a lipase enzyme produced by conventional fermentation of a naturally-occurring or non-genetically engineered organism, which is to be subjected to a denaturation treatment, it is believed that the presence of a chaperone molecule in the subsequent renaturation treatment is critical.

Accordingly, in a further general aspect the invention relates to a process for denaturating and renaturating a lipase enzyme, the process comprising (a) subjecting a lipase enzyme to a denaturation treatment, (b) mixing the denatured lipase enzyme obtained in step (a) with a chaperone molecule which has optionally been subjected to a denaturation treatment, and (c) subjecting the mixture of step (b) to renaturation to produce the active lipase enzyme.

Alternatively, the denaturation/renaturation treatment of the lipase enzyme may be carried out by a) mixing a lipase enzyme to be subjected to the denaturation and renaturation treatment with a chaperone molecule, and b) subjecting the mixture of step a) to denaturation followed by renaturation so as to produce an active lipase enzyme.

DESCRIPTION OF THE DRAWINGS

The present invention is described in the following with reference to the appended drawings, in which.

| A & S | molecular weight markers; 45, 36, 24 and 20 | | |
|---|---|---|---|
| B | pJW2 (vector) | | |
| C | pSJ150 (original lipase construct in pUC) | | |
| D | pAHE2 | 30° C. | 1.0 hours(hr) |
| E | pAHE2 | 42° C. | 1.0 hrs |
| F | pAHE2 | 42° C. | 1.5 hrs |
| G | pAHE2 | 42° C. | 2.0 hrs |
| H, M, R | purified lipase from P. cepacia | | |
| I | pAHE10 | 30° C. | 1.0 hrs |
| J | pAHE10 | 42° C. | 1.0 hrs |
| K | pAHE10 | 42° C. | 1.5 hrs |
| L | pAHE2 | 42° C. | 2.0 hrs |
| N | pCBE6 | −IPTG | 1.0 hrs |
| O | pCBE6 | +IPTG | 1.0 hrs |
| P | pCBE6 | +IPTG | 1.5 hrs |
| Q | pCBE6 | +IPTG | 2.0 hrs |

Figure 10:
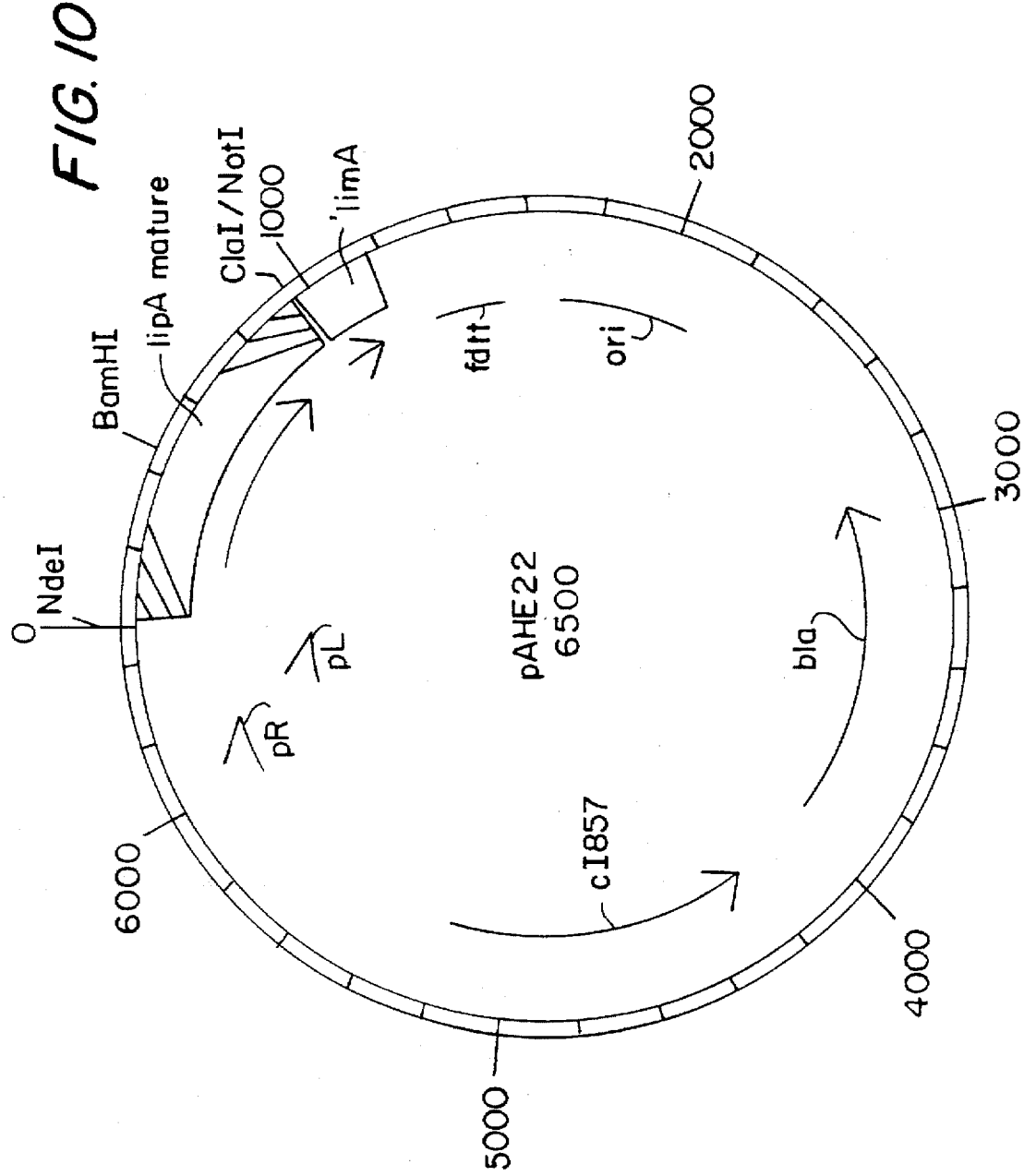

FIG. 10 shows the result of an immunoblot analysis performed as described in Example 3 using Lip antibody, in which lanes:

| A | pJW2 (vector) | | |
|---|---|---|---|
| B | pSJ150 | | |
| C | pAHE2 | 30° C. | 1.0 hr |
| D | pAHE2 | 42° C. | 1.0 hr |
| E | pAHE2 | 42° C. | 1.5 hrs |
| F | pAHE2 | 42° C. | 2.0 hrs |
| G, L, Q, S | purified lipase from P. cepacia (1OLU) | | |
| H | pAHE10 | 30° C. | 1.0 hr |
| I | pAHE10 | 42° C. | 1.0 hr |
| J | pAHE10 | 42° C. | 1.5 hrs |
| K | pAHE10 | 42° C. | 2.0 hrs |
| M | pCBE6 | −IPTG | 1.0 hr |
| N | pCBE6 | +IPTG | 1.0 hr |
| O | pCBE6 | +IPTG | 1.5 hrs |
| P | pCBE6 | +IPTG | 2.0 hrs |
| R | pAHE2 + pAHE10 | | 42° C., 1.5 hrs. |

Figure 11:
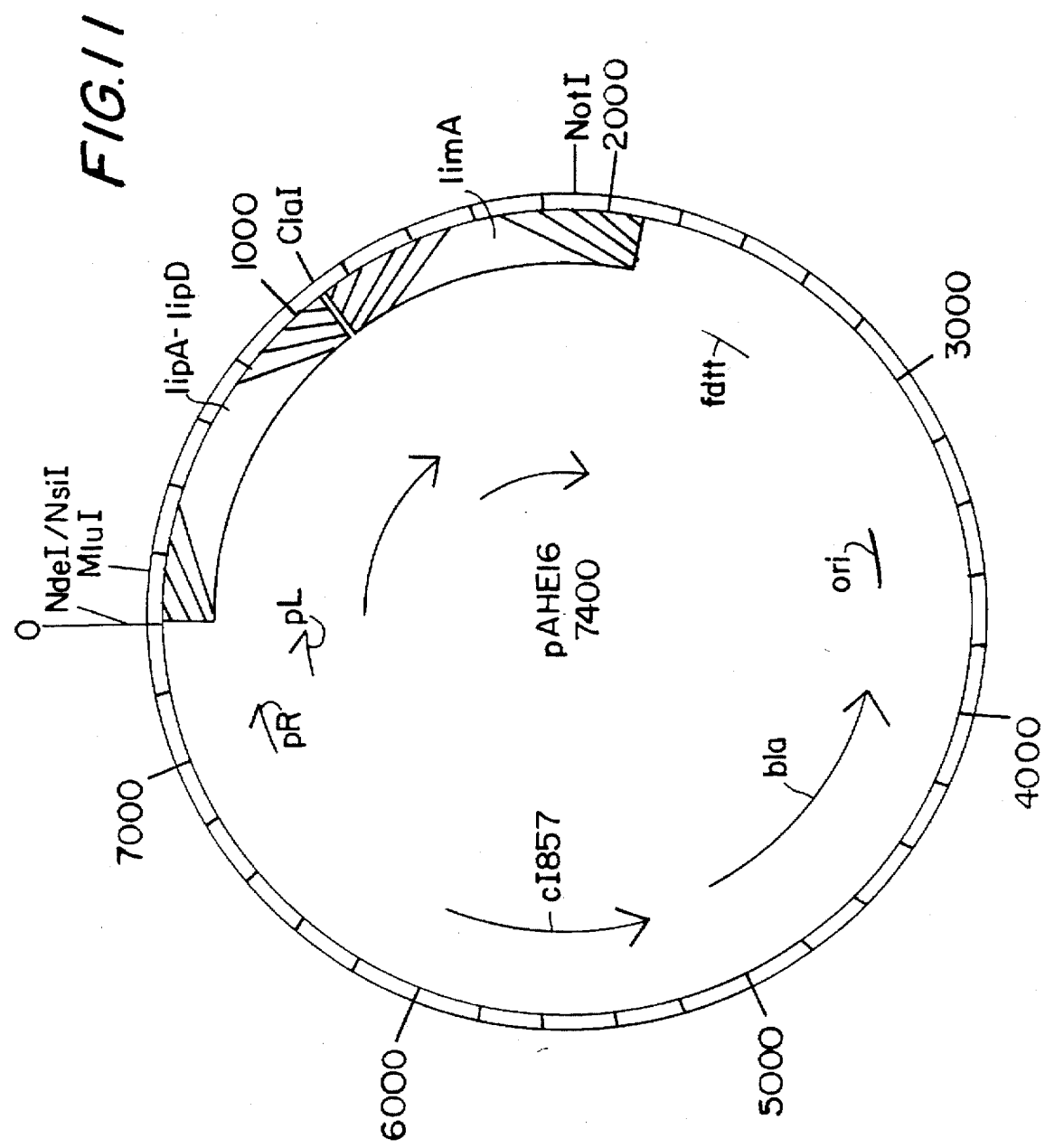

FIG. 11 illustrates the cellular localization of Lima in P. cepacia as determined by an immunoblot analysis of lipase (FIG. 11a) and Lim (FIG. 11b) induced with oleyl alcohol in intracellular (cytoplasm and inner cell membrane), periplasmic and extracellular fractions of P. cepacia (Example 7). Equal amounts of protein were loaded in each lane corresponding to 0.01, 17 and 21%, respectively. In (a) (Lipase immunoblot) the lanes contained:

| A | purified lipase from P. cepacia |
|---|---|
| B | intracellular fraction |
| C | periplasmic fraction |
| D | extracellular fraction, | in (b) (Lim immunoblot) the lanes contained:

| A | lim expressed from pJ38 |
|---|---|
| B | intracellular fraction |
| C | periplasmic fraction |
| D | extracellular fraction; |

Figure 9:
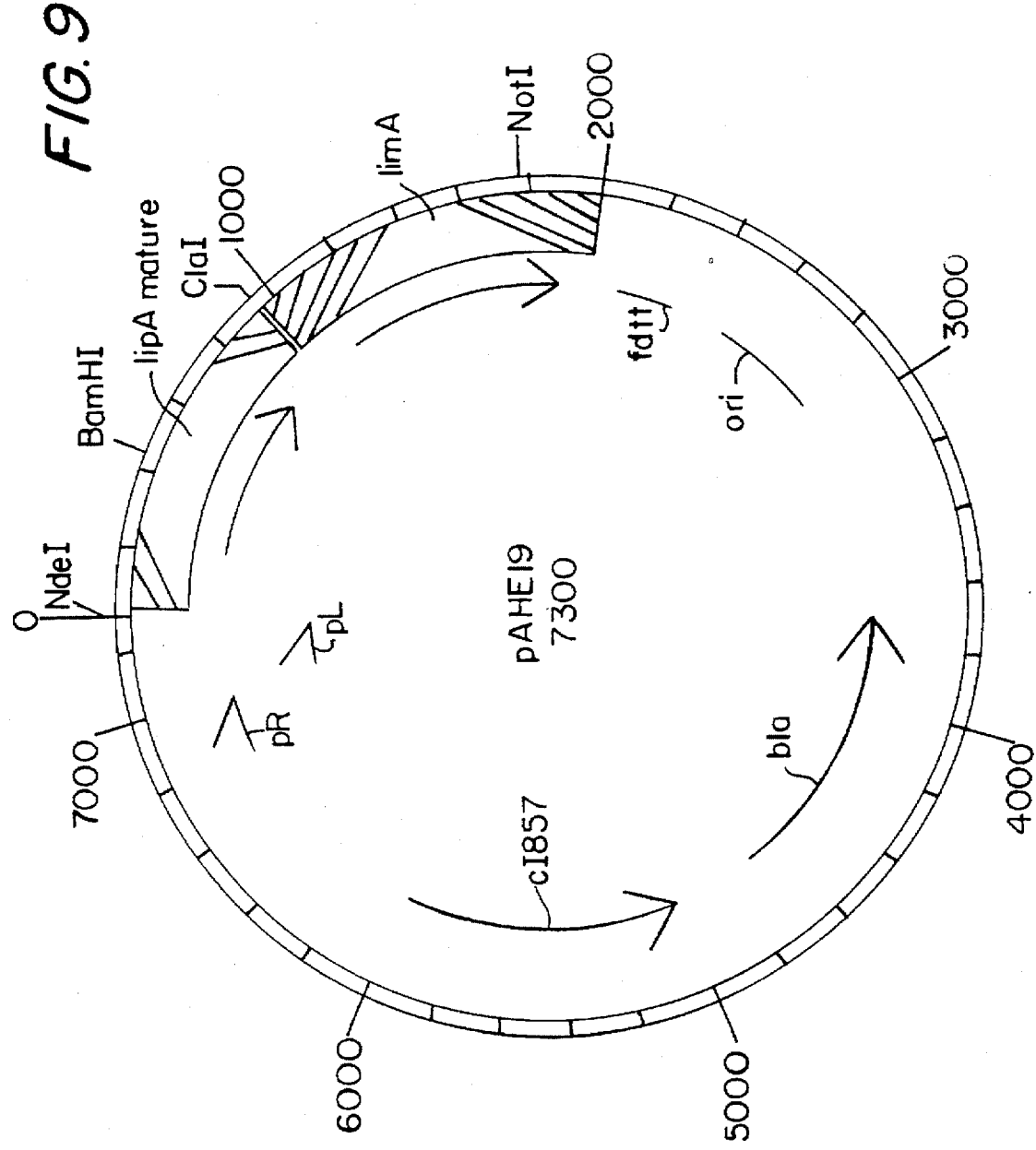
FIG. 9 shows the result of a SDS-PAGE analysis of proteins expressed in E. coli JA221 performed as described in Example 3, in which lanes.
Figure 12:
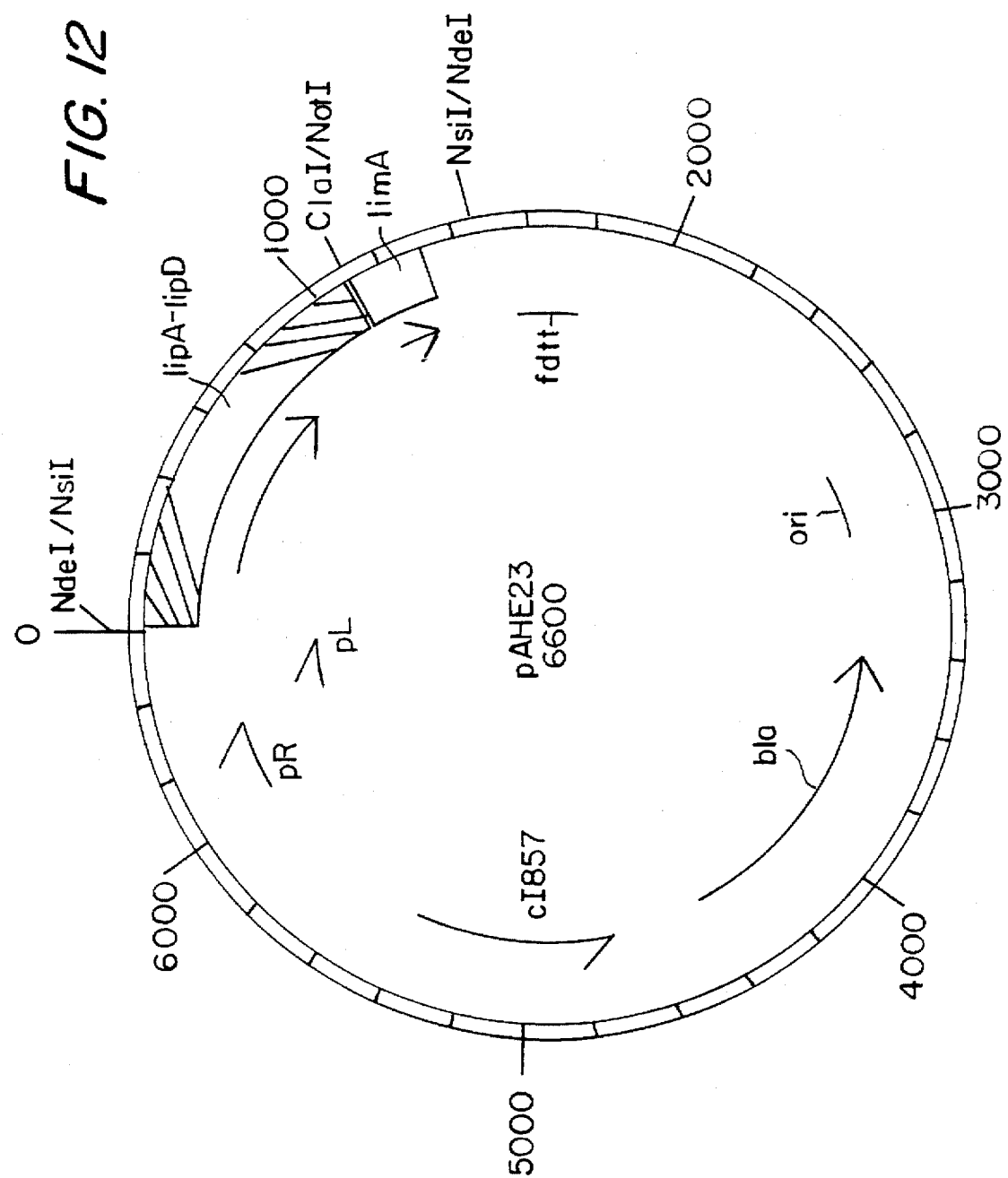

FIG. 9 illustrates the plasmid pAHE19;

FIG. 10 illustrates the plasmid pAHE22;

FIG. 11 illustrates the plasmid pAHE16;

FIG. 12 illustrates the plasmid pAHE23; and

Figure 13:
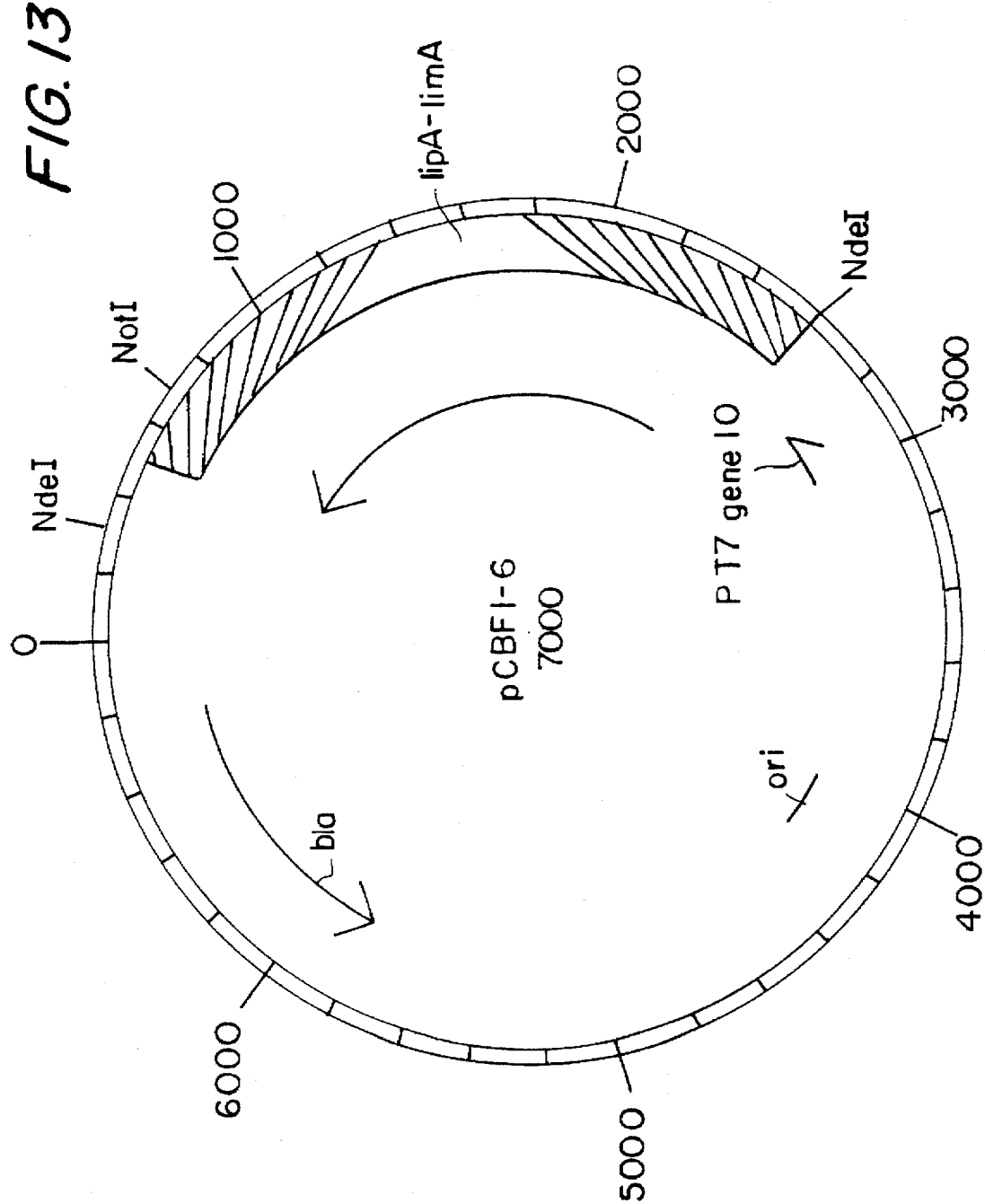

FIG. 13 illustrates the plasmid pCBF1-6.

The present invention is further illustrated in the following examples which are not in any way intended to limit the scope of the invention as claimed.

MATERIALS AND METHODS

Bacterial Strains

E. coli TG1 supE hsd-5 thi-(lac-proAB) F'[traD36proAB+ lacIq lacZ-M15] (Gibson, 1984)

E. coli JA221 (Clarke et al., J. Mol. Biol., Vol. 120, pp. 517–34 (1978)) E. coli BL21(DE3) B strain lysogen, placUV5-T7 RNApol (IPTG inducible) (Studier, 1990)

Plasmids pSJ150—Jørgensen et al., J.Bacteriol., Vol. 173, pp. 559–67 (1991))

pJW2—Wang et al., Vol. 18, p. 1070 (1990)

pET3a—Rosenberg et al., Gene, Vol. 56, pp. 125–35 (1987)

pT7-7—Obtained from Stan Tabor, Dept. of Biol. Chem., Harvard Medical School pLysE and pLysS—pACYC184::T7 lysozyme from ptet and opposite orientation (Studier, 1990).

General Methods

Standard DNA manipulations were performed essentially as described in Sambrook et al., *Molecular Cloning: A Laborator Manual*, Cold Spring Harbor (1989).

Restriction enzymes, T4 DNA ligase, DNA Polymerase I (Klenow fragment) were obtained from Boehringer Mannheim or Promega and used as recommended by the supplier.

Chicken egg white lysozyme was obtained from Sigma.

Preparation of plasmids and transformation of *E. coli* was carried out as described in Sambrook et al., *Molecular Cloning: A Laboratory Manual*, Cold Spring Harbor (1989).

SDS-polyacrylamide gels were prepared, electrophoresed and stained as described in Sambrook et al., *Molecular Cloning: A Laboratory Manual*, Cold Spring Harbor (1989).

Protein molecular weight markers were purchased from Sigma.

Lipase analysis

Lipase activity was detected on plates containing either glycerol tributyrate or an olive oil emulsion and brilliant green. Lipase activity was measured by a pH-stat method using glycerol tributyrate as substrate. 1 LU (lipase unit) is the amount of enzyme which liberates 1 μmole titratable butyric acid per minute under the following conditions:

Temperature 30.0° C.

pH 7.0

Emulsifier Gum Arabic, 1 g/l

Substrate Glycerol tributyrate, 50 ml/l (Jørgensen et al., J.Bacteriol., Vol. 173, pp. 559–67 (1991))

A lipase screening assay was performed in microtiter dishes according to the following procedure:

First an emulsification reagent is made up: 17.9 g NaCl+ 0.41 g $KH_2PO_4$+6.0 g Gum Arabic+540 ml glycerol is brought to a final volume of 1000 ml with demineralized water.

The lipase assay reagent is made up as follows: 12.5 ml of the above emulsification reagent+3.75 ml of glycerol tributyrate+0.25 ml Brilliant green (40 mg/ml in $H_2O$)+50 ml of 10 mM Tris pH 9.0 is emulsified for 1 min in an Ultra Turrax emulsifier.

The actual assay is performed by mixing 100 μl of this assay reagent with 100 μl of the lipase sample. The color development is compared to that of a known lipase sample.

The brilliant green plates consisted of 15 ml LB agar, with a top layer of 3 ml LB agar containing 0.3 ml of a 10% olive oil emulsion and 0.1 ml of a 40 mg/ml solution of brilliant green in distilled water. The olive oil emulsion was olive oil 10 ml+Gum Arabic 1 g+deionized water 90 ml, mixed using an Ultra Turrax emulsifier.

Induction of *E. coli* cultures for high level expression (a) pJW2 based plasmids Overnight cultures were grown at 30° C. in an orbital shaker at 250 rpm, diluted 1:100 and grown for 3–4 hrs at 30° C. until an A600 of 0.5 was reached. One of a set of duplicate cultures was then shifted to 42° C. for induction of protein synthesis. Samples from both cultures were taken at time=0, 30, 60, 90 and 120 minutes after induction.

(b) pET3a/pT7-7 based plasmids

Overnight cultures were grown at 37° C. in an orbital shaker at 250 rpm, diluted 1:50 and grown at 37° C. until an A600 of 0.5 was reached. IPTG was then added to a final concentration of 1.5 mM to one of a set of duplicate cultures. Rifampicin may also be added to the induced culture 15 min after IPTG addition to a final concentration of 100 μg/ml. Samples from both cultures were taken at time=0, 30, 60, 90 and 120 minutes after induction.

Treatment and preparation of protein samples

Samples were immediately cooled to 0° C. Cells were harvested by centrifugation in a microfuge at 12,000 g for 5 min at 4° C. Cell pellets were resuspended in Laemmli sample buffer and frozen at −20° C. Proteins were precipitated from the supernatants by addition of an equal volume of acetone and leaving on ice for 30 min followed by centrifugation for 15 min at 12,000 g at 4° C. The precipitated proteins were resuspended in Laemmli sample buffer and frozen at −20° C.

Analysis of proteins by SDS-polyacrylamide gel electrophoresis

Protein samples were boiled for 5 min prior to loading on 12% SDS-polyacrylamide gels. The gels were electrophoresed in Tris-glycine until the dye front reached the gel end and were then stained in 0.25% coomassie brilliant blue and destained in 10% acetic acid.

Western analysis

The method used was equivalent to that of Towbin et al. (1979). Protein samples were electrophoresed in 12% SDS-polyacrylamide gels and electrophoretically transferred to nitrocellulose. Filters were preincubated with blocking buffer and then incubated with anti-lipase antibody. Alkaline phosphatase-conjugated goat anti-rabbit IgG (Sigma) was then incubated with the filter. NitroBlue Tetrazolium and 5-bromo-4-chloro-indolyl phosphate (both from Sigma) were used to visualize the proteins.

Method for Cell Lysis: adapted from Marston, In DNA Cloning: A practical approach (ed D.M. Glover), Vol. 3, p. 59. IRL Press, Oxford (1987)

Overnight cultures were diluted 1:100 into 100 mls LB medium and grown to an OD600 value of 0.5. Induction with heat in the case of pAHE2 and pAHE10 and IPTG in the case of pCBE6 was carried out for 2 hours. The cultures were then centrifuged at 500 g for 15 minutes at 4° C. The supernatant was removed and the pellet was weighed. For each gram (wet weight) of *E. coli* cells, 3 ml of lysis buffer was added and the pellet was resuspended. Lysis Buffer contained 50 mM Tris. Cl, 1 mM EDTA, 100 mM NaCl.

For each gram of cells, 8 ml of a 50 mM PMSF stock and 80 μl of lysozyme (10 mg/ml) was added and stirred for 20 minutes. 4 mg of deoxycholic acid was added per gram of cells while stirring continuously. The lysate was placed at 37° C. and stirred with a glass rod. When the lysate became viscous 20 μl of DNAaseI (1 mg/ml) was added per gram of cells. The lysate was placed at room temperature until it was no longer viscous (approx 30 minutes). The cell lysate was then stored at 4° C. until required.

Purification and washing of inclusion bodies: (Marston et al., BioTechnology, Vol. 2, p. 800 (1984))

The cell lysate was centrifuged at 12000 g for 15 minutes at 4° C. The supernatant was decanted and the pellet was resuspended in 9 volumes of lysis buffer containing 0.5% Triton and 10 mM EDTA (pH 8.0). Storage at room temperature for 5 minutes was followed by centrifugation at 12000 g for 15 minutes at 4° C. The supernatant was decanted and set aside and the pellet was resuspended in 100 μl of $H_2O$. 10 μl samples were removed from the supernatant and the resuspended pellet and were mixed with 10 μl of 2×SDS gel loading buffer and analyzed by SDS-polyacrylamide gel electrophoresis to determine if most of the protein of interest is in the pellet. The lipase screening assay was also carried out to determine if most of the lipase activity of pAHE2 was in the pellet fraction.

Solubilization of inclusion bodies and renaturation: (adapted from Marston et al., BioTechnology, Vol. 2, p. 800 (1984))

100 μl of lysis buffer containing 0.1 mM PMSF (added fresh), 8M Urea (deionized), and 0.1M beta-mercaptoethanol was added to the washed pellet and stored for 1 hour at room temperature. The lipase activity screening assay was carried out in order to observe whether the lipase activity had disappeared due to the protein being totally denatured. 50 μl of each of the denatured protein samples were placed in dialysis tubing. The protein samples were dialyzed in a buffer of 50 mM KH2PO4 (pH10.7), 1 mM EDTA (pH 8.0), 50 mM NaCl and which also contained 8M urea and 0.1M BME. The pH was maintained at 10.7 with KOH. Initial dialysis in 8M urea was carried out overnight. Further dialyses using a lower concentration of urea (ie 6M; 4M; 2M; 0M) were carried out in the above buffer in the absence of BME. The pH in these dialysis reactions was maintained at 8.0 using HCl. Dialysis in each of the different concentrations of urea was allowed to take place for 6 hours. As a control experiment duplicate samples were dialyses exactly as above except in the absence of urea and BME.

The renatured samples were removed from the dialysis tubing and lipase activity of the samples was examined on glycerol tributyrate and brilliant green plates. The lipase activity was also examined using the microtiter lipase screening assay.

Recovery of proteins from SDS-polyacrylamide gels

The procedure for recovering proteins from SDS-polyacrylamide gels was described by Hager et al., Anal. Biochem., Vol. 109, pp. 76–86 (1980). Protein samples were electrophoresed on an SDS-polyacrylamide gel. After electrophoresis, the gel was removed into a tray, rinsed with water and stained for 10 minutes with ice-cold 250 mM KCl and 1 mM DTT. The gel was destained in cold water containing 1 mM DTT and the protein band of interest was cut out. (A portion of the gel was stained with coomassie blue to stain molecular weight standards to ensure the correct band was cut out). The gel band was crushed through a 1 ml syringe with G18 needle and 1 ml of elution buffer containing 0.1% SDS, 50 mM Tris/HCl (pH 7.9), 0.1 mM EDTA, 5 mM DTT, and 200 mM NaCl, was added. The protein was allowed to elute for at least 1 hour at 25° C. with occasional agitation. The mixture was centrifuged briefly to pellet the crumbled gel. The protein was precipitated from the supernatant by adding 4 volumes of cold acetone and incubating at −70° C. for 20 min. The precipitated protein was centrifuged and the pellet was allowed to dry.

Generation of anti-LimA anti-sera in rabbits

In order to raise antibodies against LimA, three rabbits were injected with purified Lima protein according to a schedule similar to that described by Vaitukaitis, Methods in Enzymology Vol. 21, pp. 46–52 (1981). The LimA protein was purified from preparative SDS-polyacrylamide gels. On day 1, Lim in 10 mM sodium phosphate, pH 7.2 was mixed with complete Freunds adjuvant and injected intradermally at 10 sites in the back of each rabbit. On day 21 a booster injection, mixed with incomplete Freunds adjuvant, was injected intramuscularly into the leg of each rabbit. An identical booster was injected in the same way on day 31 of the schedule. A test bleed revealed that anti-Lim antibodies had been generated.

Media

LB per liter:

10 g bacto-tryptone 5 g bacto-yeast extract 10 g NaCl

Plates contained 2% agar.

EXAMPLES

Example 1

Constructions for high level LipA expression (a) lipA+limA: pAHE2 and pAHE8

Figure 1:
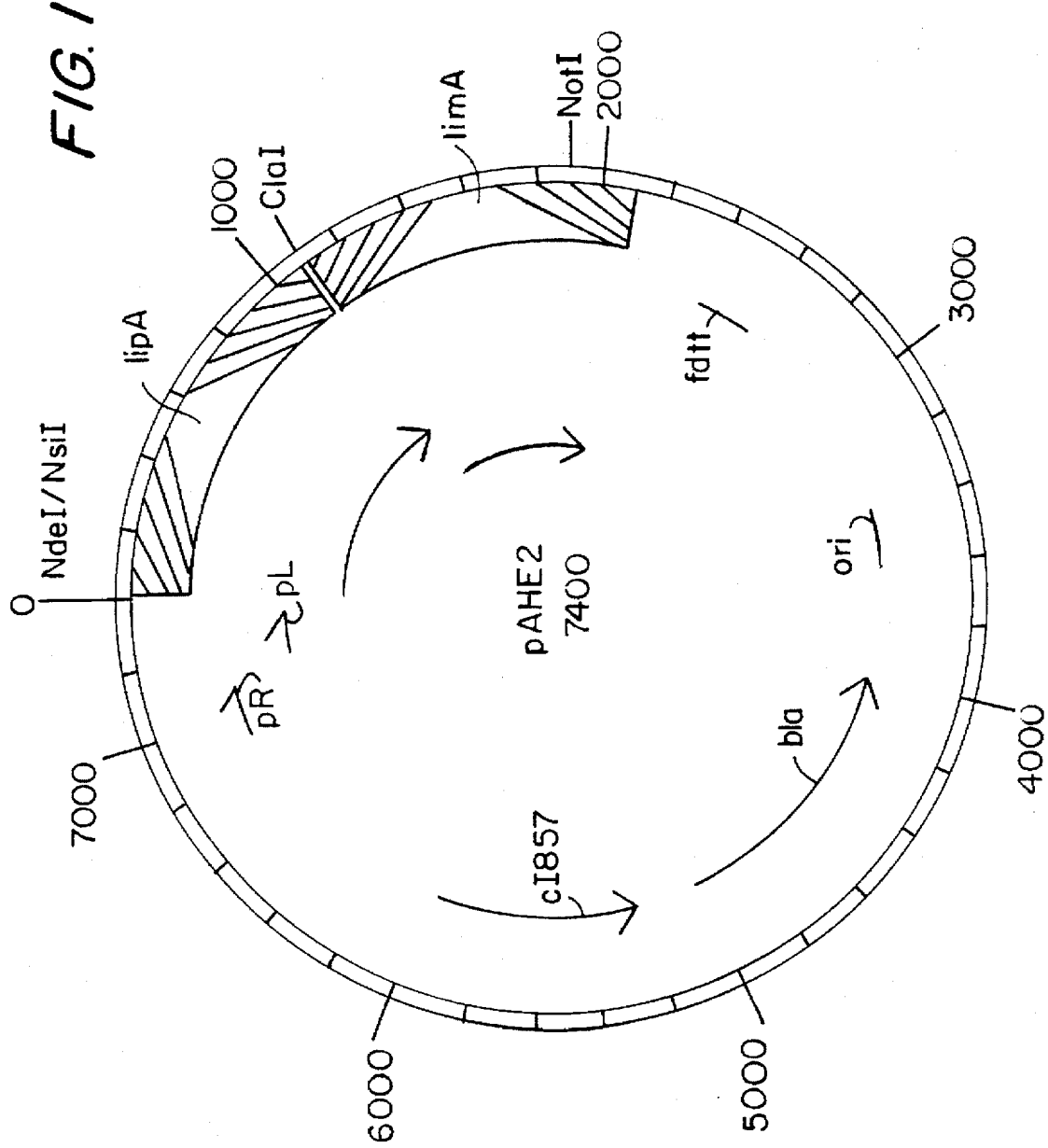
FIG. 1 illustrates the plasmid pAHE2.

Plasmid pAHE2 (FIG. 1) was constructed by subcloning the 2.264 kb NsiI fragment encoding both lipA+limA from pSJ150 (Jørgensen et al., J. Bacteriol., Vol. 173, pp. 559–67 (1991)) into NdeI-digested pJW2 (Wang et al., Vol. 18, p. 1070 (1990)). Ligations were transformed into E. coli TG1 at 30° C. and plasmid DNA mini-preparations were used to identify plasmids with insert in the correct orientation. pAHE2 is one of a few correct constructs obtained. In pAHE2 the initiation codon of the lipase gene is immediately downstream from the phage T7 ribosome binding site.

E57 is E. coli strain JA221 transformed with pAHE2. When E57 is induced for high level protein production, lipase protein can be identified on SDS-polyacrylamide gels (and by western analysis) and lipase activity can be detected on brilliant green and glycerol tributyrate plates and by the microtiter assay and by pH-stat method.

Figure 2:
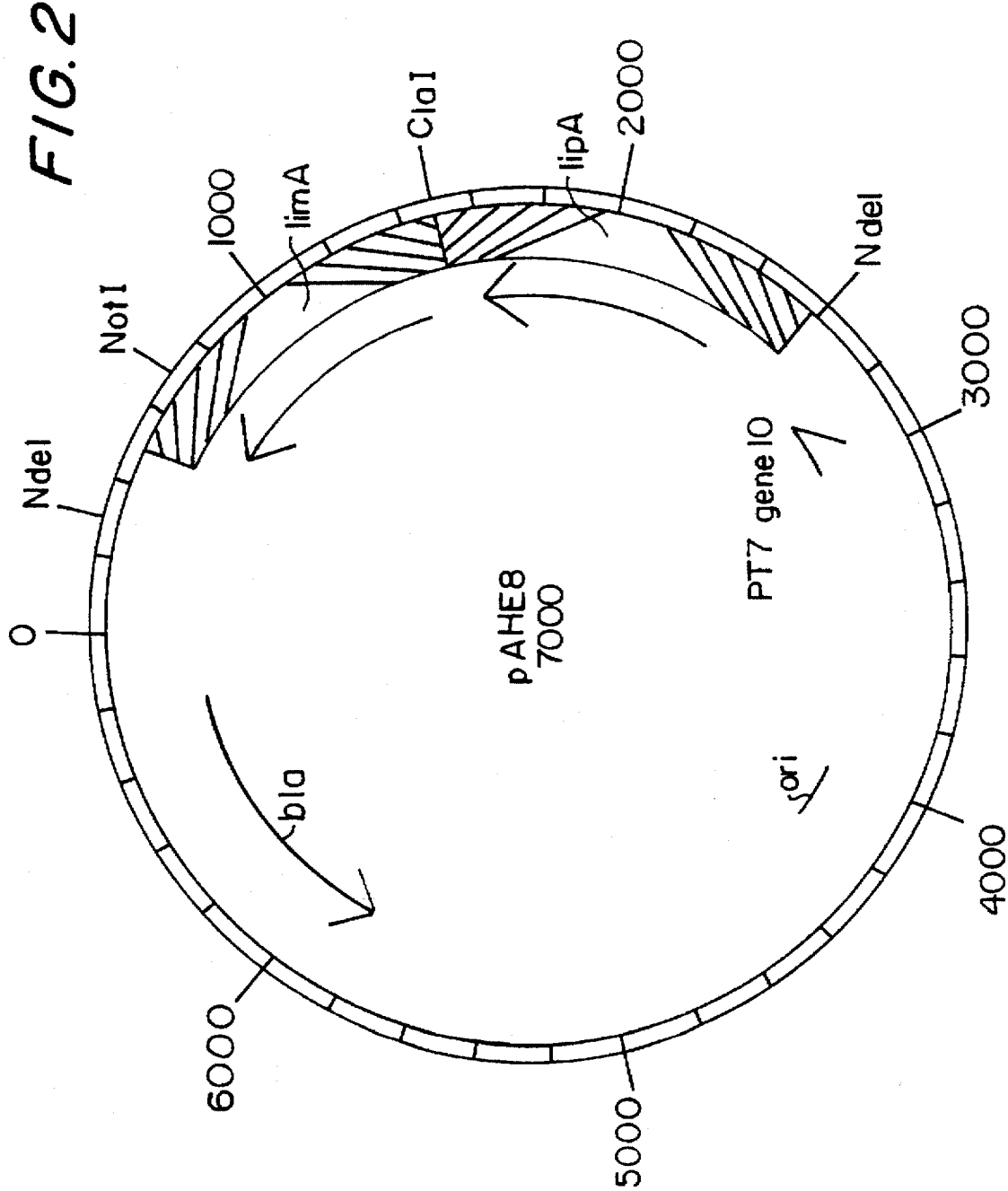
FIG. 2 illustrates the plasmid pAHE8.

Plasmid pAHE8 (FIG. 2) was constructed by subcloning the 2.264 kb NdeI fragment encoding lipa+limA from pAHE2 into the expression vector pET3a digested with NdeI. Ligations were transformed into E. coli strain TG1 and plasmid DNA was prepared from transformants to identify the correct plasmids.

E73 is E. coli strain BL21(DE3) pLysS transformed with pAHE8. When E73 is induced for high level protein production, lipase protein (approx. MW 34 kD) can be seen on SDS-polyacrylamide gels and lipase activity is detected on brilliant green and glycerol tributyrate plates and by the microtitre assay.

(b) lipA without limA: pAHE10

Figure 3:
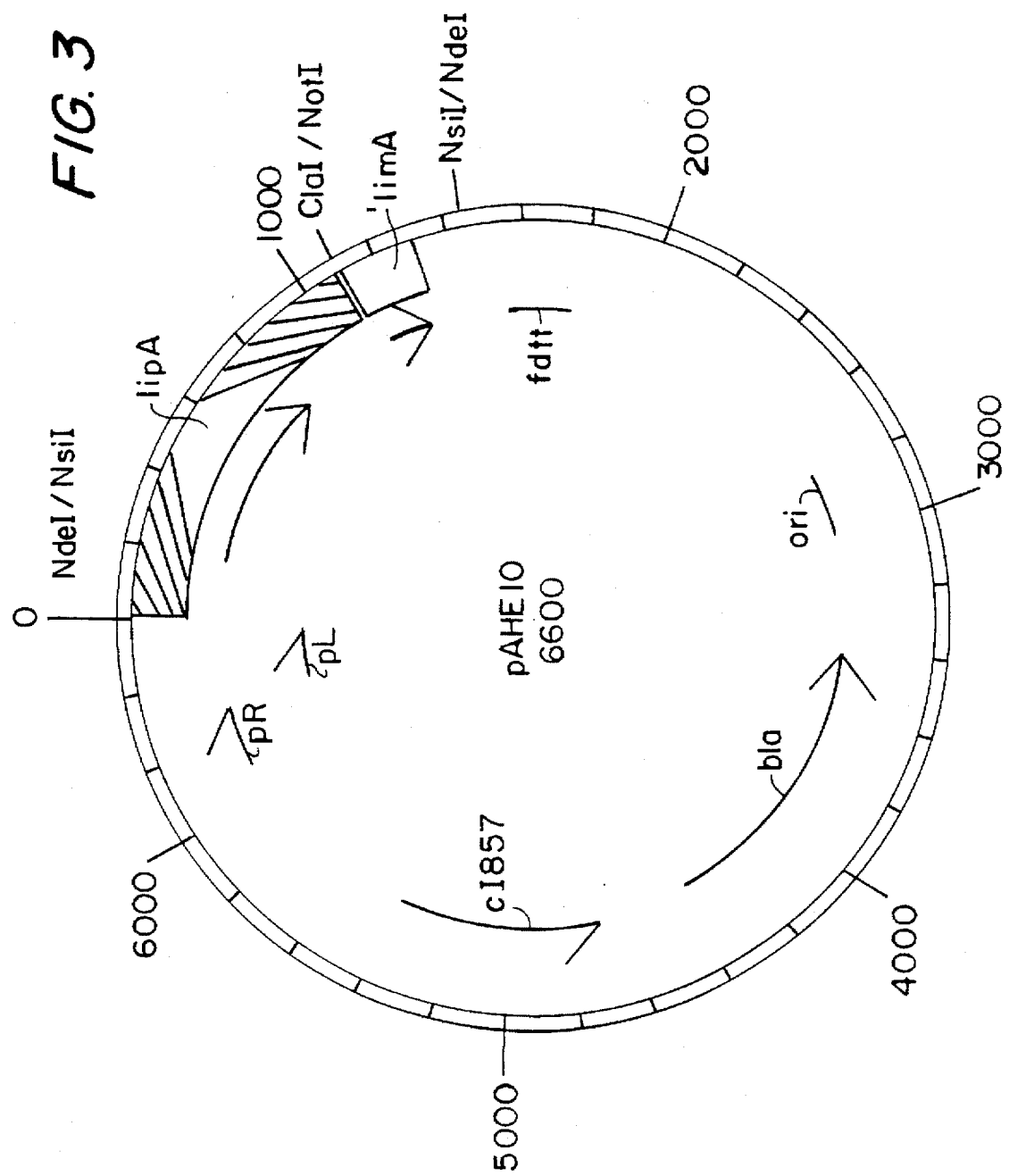
FIG. 3 illustrates the plasmid pAHE10.

Plasmid pAHE10 (FIG. 3) is a derivative of pAHE2 from which ⅔rds of the coding region of the limA gene was deleted. Plasmid pAHE10 was constructed by digesting pAHE2 with the restriction enzymes ClaI and NotI, followed by treatment with Mung Bean Nuclease. DNA of the size 6.3 kb was excised as a band from an agarose gel stained with ethidium bromide. The DNA was purified using a Gene Clean kit, ligated and transformed into competent E. coli TG1. Plasmid DNA mini-preparations were used to identify the correct clones.

E68 is E. coli JA221 transformed with pAHE10. When E68 is induced for high level protein production, lipase protein, in comparable quantities to that from pAHE2, can be seen on SDS-polyacrylamide gels and by western analysis, but no lipase activity can be detected.

Example 2

Constructions for high level LimA expression: pCBE6, pCBE7, pCBE12, pCBE18 and pCBE19

Figure 4:
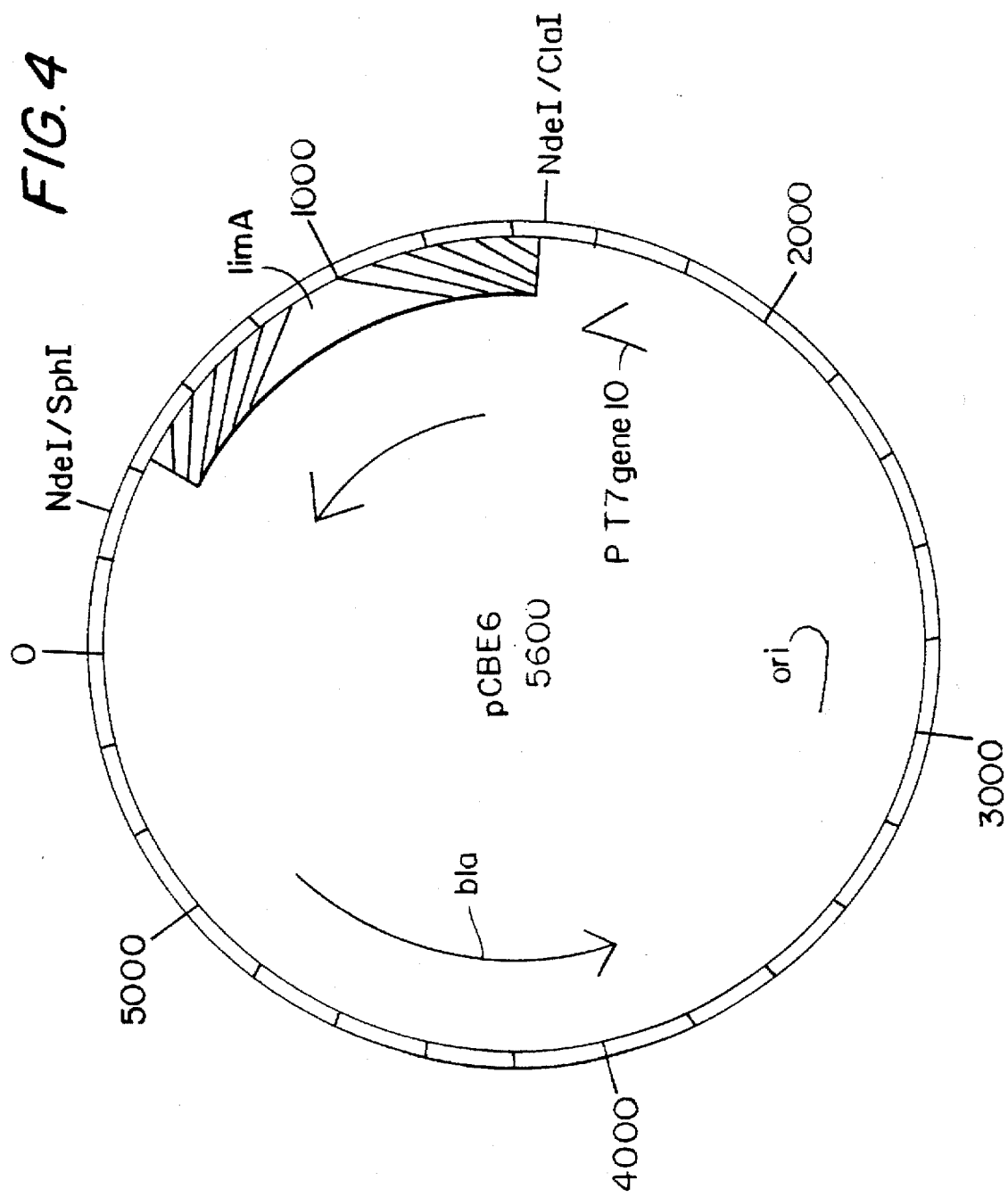
FIG. 4 illustrates the plasmid pCBE6.

Plasmid pCBE6 (FIG. 4), from which limA alone is expressed, was constructed by subcloning the 1.17 kb ClaI-SphI fragment from pSJ150 as a blunt-ended fragment into the expression vector pET3a digested with NdeI and treated with Klenow to generate blunt ends. E. coli strain E102 is strain BL21 (DE3)pLysS transformed with pCBE6.

Figure 5:
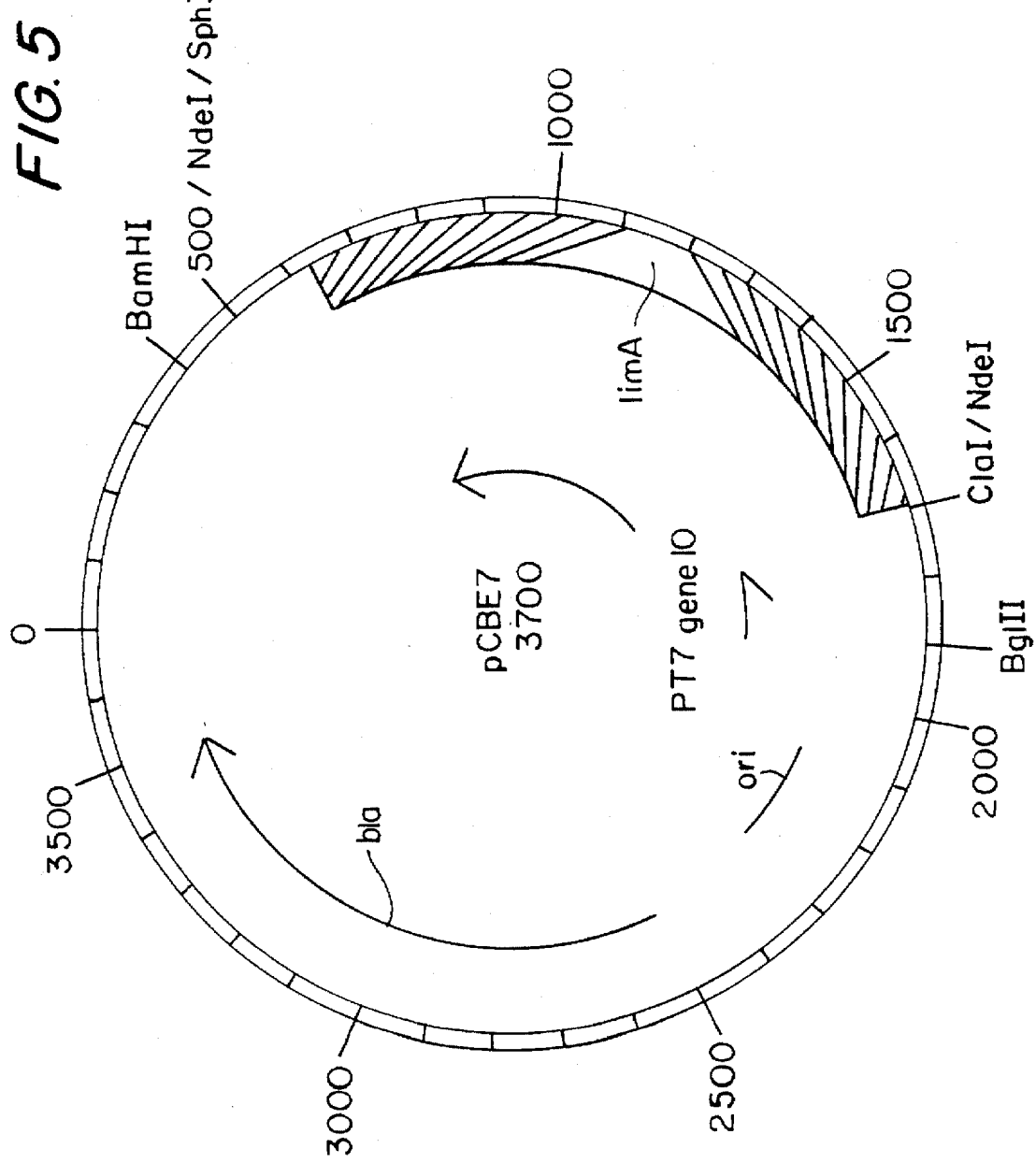
FIG. 5 illustrates the plasmid pCBE7.

Plasmid pCBE7 (FIG. 5) was constructed by subcloning the same 1.2 kb ClaI-SphI fragment into the expression vector pT7-7. E103 is BL21(DE3) pLysS transformed with pCBE7. Upon induction of E102 and E103, a protein of molecular weight approx. 32 kD was observed.

Figure 6:
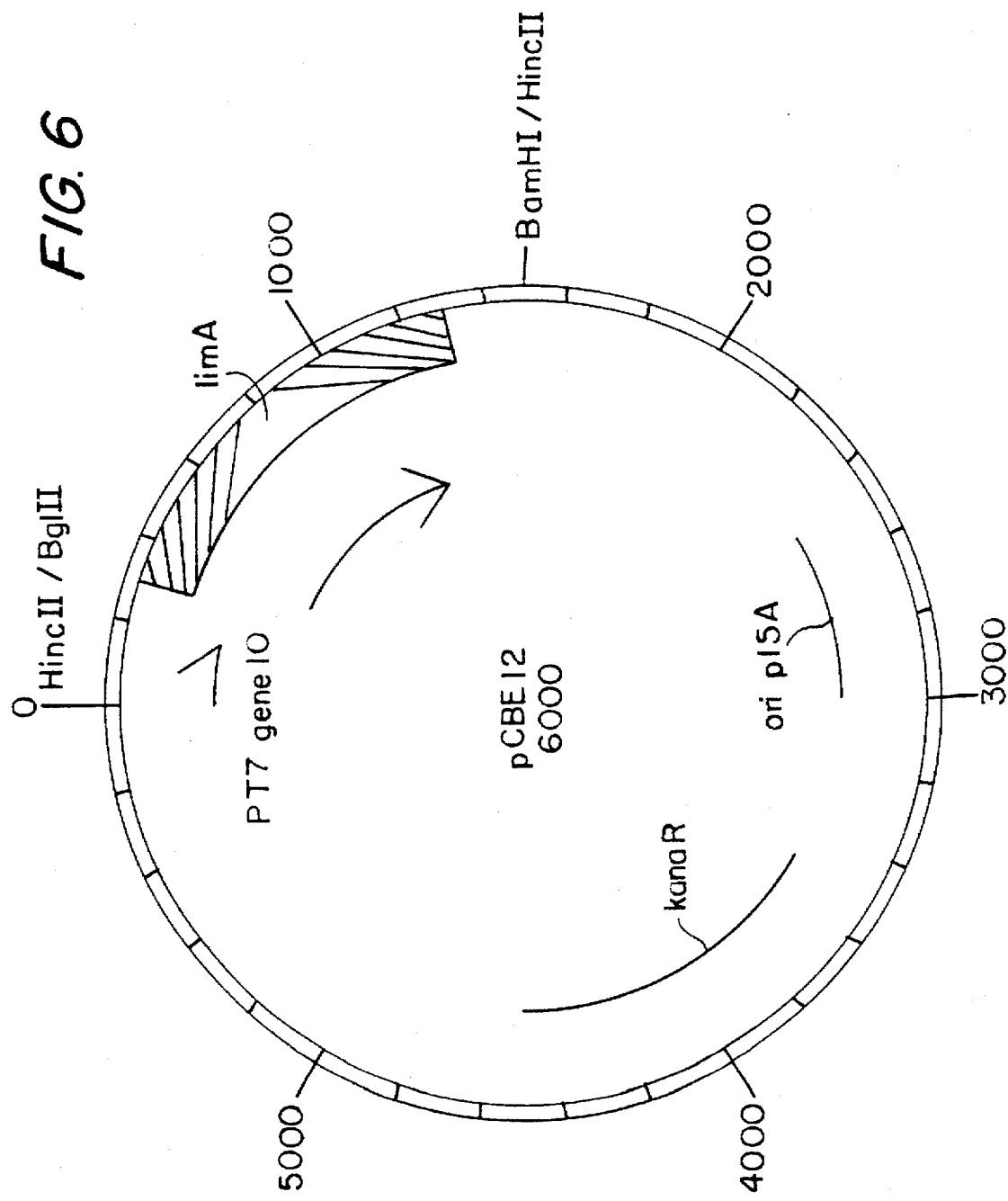
FIG. 6 illustrates the plasmid pCBE12.

Plasmid pCBE12 (FIG. 6) was constructed by subcloning the BglII-BamHI fragment of pCBE7 into pACYC177. Lim expressed from pCBE12 in trans to lipase expressed from pSJ518 (described in FIG. 3 of WO 90/00908) and pAHE10 gives rise to lipase activity.

Figure 7:
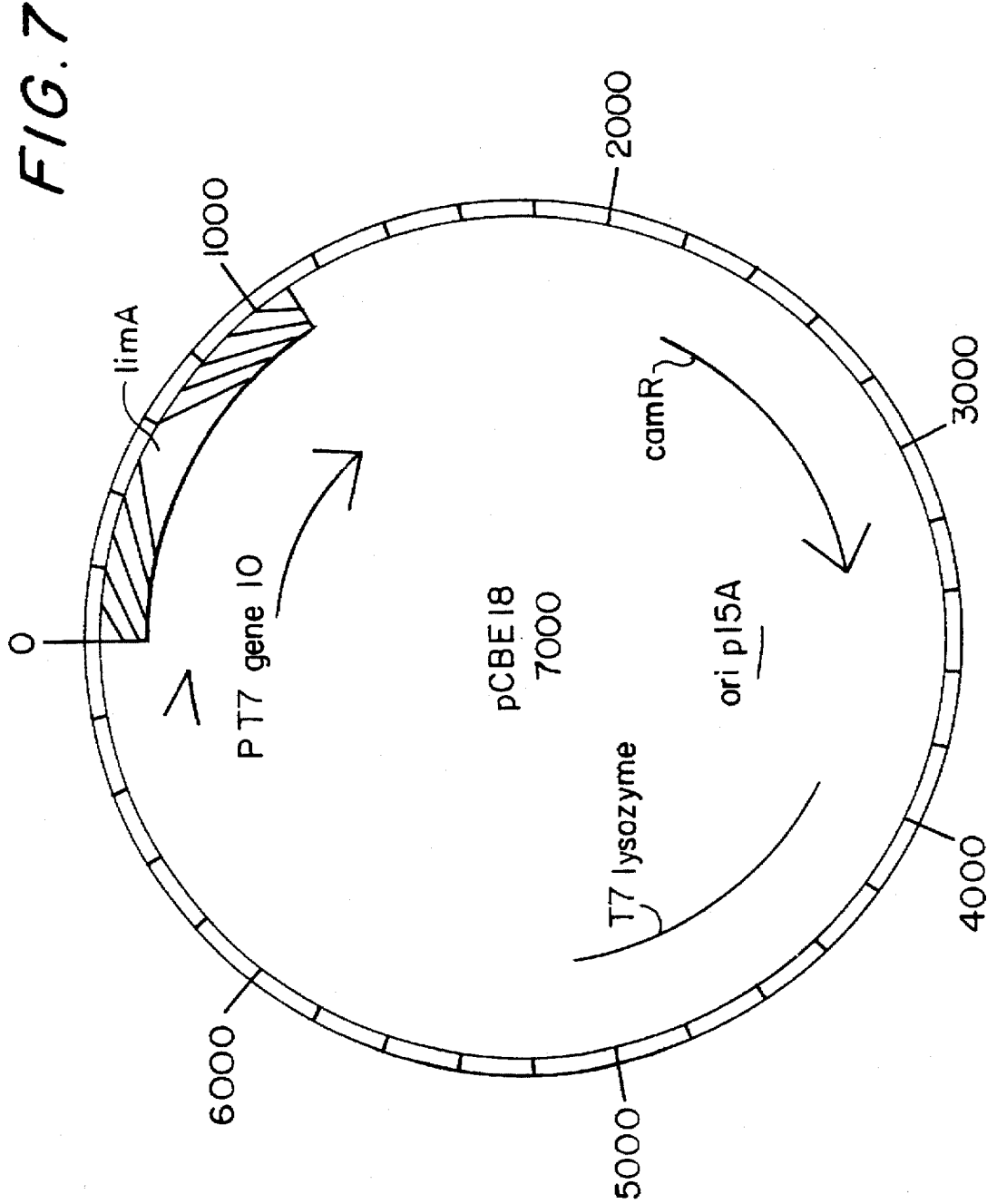
FIG. 7 illustrates the plasmid pCBE18.
Figure 8:
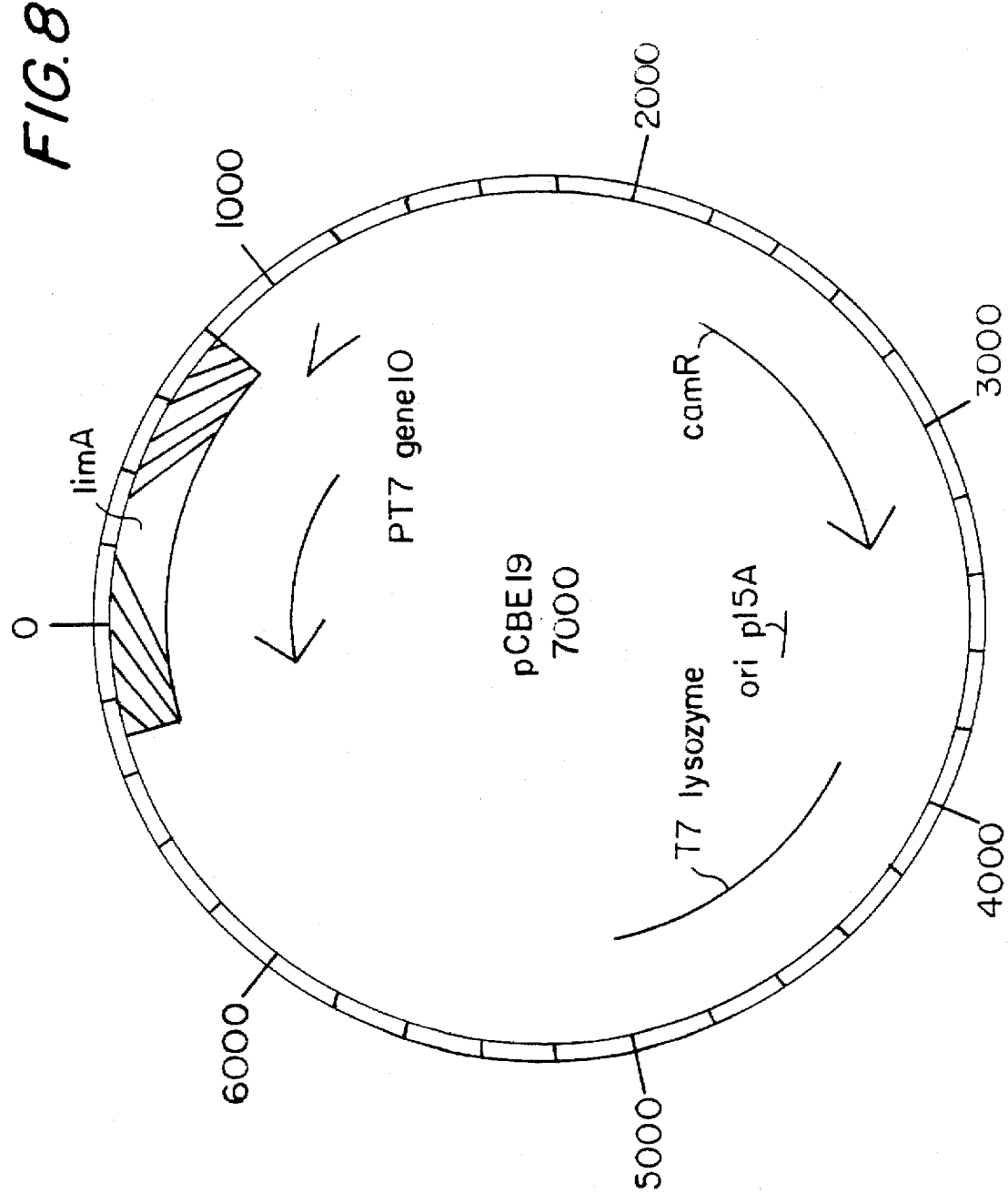
FIG. 8 illustrates the plasmid pCBE19.

Plasmids pCBE18 and 19 (FIGS. 7 and 8) were constructed by subcloning the BglII-BamHI fragment of pCBE7 into the BclI site of pLysS. Lim expressed from pCBE18 and 19 in trans to lipase from pAHE10 gives rise to lipase activity.

Example 3

Growth/induction experiments to obtain high level protein expression

Cultures were induced to produce high levels of both LipA and Lima as follows. E. coli strains E57 (JA221/pAHE2) and E68 (JA221/pAHE10) were grown overnight at 30° C. at 250 rpm. The cultures were diluted 1:100 and grown at 30° C. at 250 rpm until the A600 was 0.5. The cultures were then shifted to grow at 42° C. E. coli strain E102 (BL21(DE3)pLysS/pCBE6) was grown overnight at 37° C., diluted 1:100 and grown until A600 was 0.5. IPTG was then added to the culture to a final concentration of 1.5 mM. Fifteen minutes later rifampicin was added to a final concentration of 100 µg/ml. The culture was incubated at 37° C. and shaken at 250 rpm throughout the growth. Samples were taken from each culture at 60, 90 and 120 minutes after induction.

Samples were analyzed by SDS-polyacrylamide gel electrophoresis and by western analysis using anti-serum raised against lipase. Lipase protein was observed to be induced in strains containing either pAHE2 or pAHE10, in equivalent amounts. The lipase for the majority about 95% is larger than the mature lipase isolated from Pseudomonas cepacia and the size is consistent with that expected for the complete prelipase. Samples were also assayed for lipase activity by the microtitre assay. Lipase activity was observed from cultures of E57 (pAHE2, lipA+limA), but none was observed from cultures of E68 (pAHE10, lipA only) or E102 (pCBE6, limA).

The results demonstrate that lipase protein is made in equivalent amounts in the presence and in the absence of the limA gene, but no lipase activity is detected in the absence of limA. Active lipase is only produced when the limA gens is also present.

Example 4

Purification of Lip and Lim

Overnight cultures of JA221/pAHE2; JA221/pAHE10; BL21/pLysS/pCBE6 and BL21 were diluted 1:100 into 100 mls LB medium and grown to an OD600 value of 0.5. Induction with heat in the case of pAHE2 and pAHE10 and IPTG in the case of pCBE6 was carried out for 2 hours. The cultures were then centrifuged at 500 g for 15 minutes at 4° C.

Cells were lysed by the method described. The Lim protein was found to be in the soluble fraction of the cell lysate. The lipase was found to reside in inclusion bodies. Inclusion bodies were prepared by a method adapted from Marston et al., BioTechnology, Vol. 2, p. 800 (1984). Pure lipase and Lim proteins were prepared after SDS-PAGE of inclusion bodies and soluble lysate fractions, respectively, by a method described by Hager et al., Anal. Biochem., Vol. 109, pp. 76–86 (1980). Samples were separated by 12% SDS-PAGE. After electrophoresis, the gel was soaked in transfer buffer (10 mM CAPS, 10% methanol, pH 11) for 20 min. The gel was electroblotted onto Problott which had been pretreated in 100% methanol (5–10 sec) and distilled water (2×1 min) and then soaked in transfer buffer. Electroblotting was carried out at 200 mA for 3 hours in transfer buffer at room temperature. The blot was removed from the sandwich, rinsed in distilled water and then in methanol (5–10 sec). The blot was then stained in Amido Black (0.1% w/v) in 1% (v/v) acetic acid, 40% (v/v) methanol for 1 min. The blot was rinsed in frequent changes of distilled water, air dried and stored at −20° C. between layers of filter paper. The bands corresponding to LimA and prelipase were excised and sequenced directly on an Applied Biosystems 477A protein sequencer.

The following sequences were obtained:

LimA (pCBE6): TARGGRAPL-RRAVVYGAVG (SEQ ID NO:6)

preLipA (pAHE2): ARTMRSRVVAGAVA-AMSIA (SEQ ID NO:7)

preLipA (pAHE10): ARTMRSRVVAGAV-AM-IA (SEQ ID NO:8)

Except for the fact that the N-terminal methionine has been cleaved off, the sequences are as expected for LimA and for preLipA as deduced from the DNA sequence.

Gel-purified LimA protein was used to raise polyclonal antibodies as described in the methods section.

The purity of the proteins was checked by further SDS-PAGE analysis.

Example 5

Denaturation and renaturation of pAHE2 and pAHE10 LipA

Denaturation/renaturation experiments were carried out with LipA from either pAHE2 or pAHE10 (present in inclusion bodies) together with LimA (pCBE6 and present in the cell lysate). 60 µl of inclusion bodies was mixed with varying volumes of pCBE6 cell lysate (0–30 µl) and solubilized together in 8M urea. Renaturation was carried out by dialysis against decreasing concentrations of urea. Experiments were carried out in the presence and absence of 5% glycerol. The lipase activity was measured using the pH stat.

The results of this experiment (shown below) indicate that increasing percentages of lipase activity may be recovered by denaturing/renaturing in the presence of increasing quantities of LimA, and that the presence of glycerol does not affect the recovery of lipase activity.

Results for pAHE2 and pAHE10 LipA

Inclusion bodies undiluted; LimA from lysate

Initial lipase activity measured for pAHE2(pJW2::lipA/limA)=7.5 LU (volume 60 µl)

Initial lipase activity measured for pAHE10(pJW2::lipA) =0 LU

| Denaturation and renaturation | | | |
|---|---|---|---|
| Sample | No of LU denatured | No of LU recovered (−Glycerol) | No of LU recovered (+Glycerol) |
| pAHE2 + 0 µl LimA | 7.5 | 5.3 | 5.3 |
| pAHE2 + 10 µl LimA | 7.5 | 9.3 | 8.3 |
| pAHE2 + 20 µl LimA | 7.5 | 12.3 | 9.0 |
| pAHE2 + 30 #1 LimA | 7.5 | 13.2 | 13.5 |

-continued

Denaturation and renaturation

| Sample | No of LU denatured | No of LU recovered (−Glycerol) | No of LU recovered (+Glycerol) |
|---|---|---|---|
| pAHE2 + non-LimA lysate, 30 μl | 7.5 | 5.0 | nd. |
| pAHE10 + 0 μl LimA | 0.0 | 0.0 | 0.0 |
| pAHE10 + 10 μl LimA | 0.0 | 6.5 | 10.5 |
| pAHE10 + 20 μl LimA | 0.0 | 8.3 | 8.5 |
| pAHE10 + 30 μl LimA | 0.0 | 16.0 | 11.0 |
| pAHE10 + non-LimA lysate, 30 μl | 0.0 | 0.0 | nd. |

Example 6

Denaturation and renaturation of pAHE2 and pAHE10 LipA

For this set of experiments the inclusion body fractions were diluted 1:10. Samples of pAHE2 and pAHE10 (Lip) inclusion bodies and pCBE6 (Lim) cell lysate were analyzed by SDS-polyacrylamide gel electrophoresis. The Biorad protein assay was used to quantify the amount of proteins used in the denaturation/renaturation experiments. 10 μl of pAHE2 inclusion bodies was determined to contain 10 μg of protein; 10 μl of pAHE10 inclusion bodies to contain 8 μg of protein; and 10 μl of pCBE6 lysate to contain 25 μg total protein.

The results of this experiment (shown below) indicate that increasing the quantity of LimA in denaturation/renaturation reactions results in initially increasing recoveries of lipase activity. Addition of further quantities of LimA to the reactions is inhibitory.

Results for pAHE2 and pAHE10 Lipases Inclusion bodies diluted 1:10; LimA from lysate

| Sample dialyses | No of lipase units recovered |
|---|---|
| pAHE2 10 μl | 0.4 |
| pAHE2 10 μl + 10 μl LimA | 5.6 |
| pAHE2 10 μl + 15 μl LimA | 5.7 |
| pAHE2 10 μl + 20 μl LimA | 4.5 |
| pAHE2 10 μl + 30 μl LimA | 9.5 |
| pAHE2 10 μl + 40 μl LimA | 3.2 |
| pAHE10 10 μl | 0.0 |
| pAHE10 10 μl + 10 μl LimA | 2.5 |
| pAHE10 10 μl + 15 μl LimA | 7.8 |
| pAHE10 10 μl + 20 μl LimA | 7.3 |
| pAHE10 10 μl + 30 μl LimA | 3.5 |
| pAHE10 10 μl + 40 μl LimA | 0.5 |

Example 7

Lipase and prelipase from Pseudomonas cepacia DSM 3959

P. cepacia DSM 3959 (the strain from which lipA and limA were cloned) was induced to produce lipase by growth in LB media supplemented with 80 g/l oleyl alcohol, and extracellular, periplasmic and intracellular fractions were isolated as described by Neu et al., J.Biol. Chem., Vol. 240, pp. 3685–92 (1965).

Immunoblots (FIG. 11) and lipase activity analysis showed that the extracellular fraction contained only active, mature lipase, whereas the intracellular fraction contained only inactive prelipase.

| Fraction | lipase activity | protein % prelipase | lipase |
|---|---|---|---|
| Intracellular | − | 100 | nd |
| Extracellular | + | nd | 100 |

When LimA was provided as an extract of E. coli BL21 (DE3) pLysS pCBE6, mature, extracellular lipase form P. cepacia could be reactivated quantitatively after denaturation/renaturation only in the presence of LimA. No lipase activity was observed when intracellular prelipase was used in a similar experiment with or without LimA, as is apparent from the following table:

| Cell fraction of P. cepacia | LU prior to denaturation | LU after renatuation |
|---|---|---|
| Intracellular fraction (prelipase) | | |
| 20 μl + 0 μl LimA | 0.0 | 0.0 |
| 20 μl + 10 μl LimA | 0.0 | 0.0 |
| 20 μl + 20 μl LimA | 0.0 | 0.0 |
| 20 μl + 30 μl LimA | 0.0 | 0.0 |
| 20 μl + 30 μl non-LimA lysate | 0.0 | 0.0 |
| Extracellular fraction (mature lipase) | | |
| 20 μl + 0 μl LimA | 1.5 | 0.0 |
| 20 μl + 10 μl LimA | 1.5 | 0.4 |
| 20 μl + 20 μl LimA | 1.5 | 0.8 |
| 20 μl + 30 μl LimA | 1.5 | 1.3 |
| 20 μl + 30 μl non-LimA lysate | 1.5 | 0.0 |

The activation of lipase but not prelipase from P. cepacia by LimA during renaturation experiments is consistent with the results using lipase proteins produced in E. coli. The E. coli lipase samples are composed of approximately 5% mature lipase and 95% prelipase. The amount of lipase activity observed before denaturation (pAHE2 only) and after renaturation (pAHE2 and pAHE10) is equivalent to approximately 5% of that expected from the total amount of lipase protein seen on SDS-PAGE.

Example 8

Constructions for expression of mature LipA protein

Plasmids from which the lipase LipA was expressed in a form lacking the signal peptide, i.e. as mature lipase, were constructed. These are pAHE19 (FIG. 9), which contains a modified version of the lipA gene encoding the mature lipase followed by the limA gene, and pAHE22 (FIG. 10), which encodes the mature lipase without limA. They were constructed as follows:

The following DNA fragment was synthesized (standard methods):

```
<MluI><HindIII
5'-CGCGTAAGCTTCACATTGAAAGGGGAGGAGAATCATGGCC-
3'-    ATTCGAAGTGTAACTTTCCCCTCCTCTTAGTACCGG-
<MluI>
GCTGGCTACGCGGCGA      -3'  (SEQ ID NO:9)
CGACCGATGCGCCGCTGCGC-5'   (SEQ ID NO:10)
```

This DNA fragment basically contains the Bacillus licheniformis amyL ribosome binding site and start codon located in front of the sequence encoding the amino acids AAGYAA (SEQ ID NO:11) from the N-terminal of the mature LipA protein.

This DNA fragment was ligated into MluI digested pSJ420 (identical to pSJ416 described in WO 90/00908, and pSJ838 was isolated as a plasmid in which the HindIII site in the synthetic DNA fragment was located proximal to the amyL promoter on pSJ420.

pSJ838 carries the amyL promoter, amyL RBS, the amyL signal peptide fused to the first 6 codons of lipA, amyL RBS, mature lipA, and limA.

By in vivo recombination from pSJ838 (essentially as described in Jørgensen et al., Gene, Vol. 96, pp. 37–41 (1990)) plasmid pSJ897 was obtained, which contains the amyL promoter, amyL RBS, and mature lipA followed by limA. Immediately upstream from the amyL RBS on pSJ897 is the recognition sequence for restriction enzyme NdeI.

pAHE19 was constructed by ligation of the 4.9 kb NdeI-EcoRI fragment of pJW2, the 0.46 kb NdeI-BamHI fragment of pSJ897, and the 2.07 kb BamHI-EcoRI fragment of pSJ150.

pAHE22 was constructed from pAHE19 by ClaI+NotI digestion and ligation following exonuclease S1 treatment to make ends blunt.

Upon induction, lipase activity was observed from *E. coli* JA221 containing pAHE19, but not from *E. coli* JA221 containing pAHE22.

Example 9

Denaturation and renaturation of mature LipA with and without LimA

Mature lipase was provided as the soluble fraction following induction, harvest, and lysis of cells as described in methods, and was used in a denaturation/renaturation experiment in the presence and absence of a LimA containing cell lysate, as described in methods.

The results of this experiment (table below) shows that mature LipA produced in *E. coli* only in the presence of LimA can be renatured to give active lipase enzyme.

pAHE19: mature LipA, LimA.
pAHE22: mature LipA.

|  | LU before denaturation | LU after renaturation |
| --- | --- | --- |
| pAHE19 (100 µl) | 0.5 | 0.5 |
| pAHE19 (100 µl) + LimA (10 µl) | 0.5 | 0.5 |
| pAHE19 (100 µl) + LimA (20 µl) | 0.5 | 0.75 |
| pAHE19 (100 µl) + LimA (30 µl) | 0.5 | 0.75 |
| pAHE19 (100 µl) + non-LimA lysate (30 µl) | 0.5 | 0.25 |
| pAHE22 (100 µl) | 0.0 | 0.0 |
| pAHE22 (100 µl) + LimA (10 µl) | 0.0 | 0.5 |
| pAHE22 (100 µl) + LimA (20 µl) | 0.0 | 0.75 |
| pAHE22 (100 µl) + LimA (30 µl) | 0.0 | 0.75 |
| pAHE22 (100 µl) + non-LimA lysate (30 µl) | 0.0 | 0.0 |

Example 10

Cloning and sequence of lipD and limD from *P. cepacia* DSM 3401

Another isolate of *P. cepacia*, DSM 3401 also called strain 75-10A, produce a lipase with similarity to LipA from DSM 3959.

Cloning and sequencing of the lipase encoding DNA from DSM 3401 (using standard methods as described in WO 90/00908) revealed two genes, hereafter referred to as lipD and limD with a relatively high homology to lipA and limA.

Due to the extreme GC content of the DNA, the sequence was difficult to determine, and there still remains some undetermined basepairs—at 4 positions in the lipD gens, and at two positions in the limD gene.

The limD start codon is positioned three basepairs downstream from the lipD stop codon, as is the case for lipA and limA.

The DNA sequence encoding lipD is given in SEQ ID NO:1, and the corresponding protein sequence in SEQ ID NO:3. The DNA sequence encoding limD is given in SEQ ID NO:2, and the corresponding protein sequence in SEQ ID NO:4.

From an alignment study of the amino acid sequences of LipA and LipD it appeared that there are 22 differences in the mature part of the enzyme, in addition to 5 positions where the LipD amino acid sequence could not be deduced.

From an alignment study of the amino acid sequences of LimA and LimD it appeared that there are 32 differences, in addition to 2 positions where the LimD amino acid sequence could not be deduced.

Based on these studies it is clear that LipD and LipA as well as LimD and LimA are homologous, but still different lipase and lipase modulator proteins.

It was therefore of interest to see if LimA could activate LipD in a denaturation/renaturation experiment.

Example 11

Denaturation/renaturation experiments with LipD purified from *P. cepacia*

LipD from strain 7510-A (=DSM3401) was provided as a partially purified protein from DSM3401, using standard protein purification methods.

Denaturation/renaturation experiments were carried out using the lipase from strain 7510-A in the presence and absence of LimA. 18 LU were denatured and renatured with varying ratios of LimA and the recovered lipase activity was measured. LipAse activity was measured on the pH-stat. As control, the experiments were also carried out in the absence of urea.

The results obtained show that when the 7510-A lipase was denatured and renatured in the absence of LimA effectively no lipase activity was recovered. When increasing levels of LimA were added to the 7510-A lipase increasing levels of lipase activity were observed. However, the percentages of lipase activity recovered were still very low.

Results for 7510-A lipase
13,000 LU/ml stock used; LimA from lysate

| Sample dialyzed | No of LU denatured | No of LU recovered (+UREA) | % recovery |
| --- | --- | --- | --- |
| 7510A 15 µl | 18 | 0.25 | 1.4 |
| 7510A 15 µl + 5 µl LimA | 18 | 0.25 | 1.4 |
| 7510A 15 µl + 10 µl LimA | 18 | 0.4 | 2.2 |
| 7510A 15 µl + 15 µl LimA | 18 | 0.35 | 2.0 |
| 7510A 15 µl + 30 µl LimA | 18 | 0.45 | 2.5 |

An explanation for the low recovery of lipase activity was later found. It turned out that the lipase in this particular preparation was degraded during denaturation/renaturation, so the experiment was repeated with a new, partly purified preparation of lipase from DSM3401 and LimA from induced BL21(DE3) pLysS pCBE6. The following results show that LimA is well able to activate LipD.

|  | LU before denaturation | LU after renaturation | % recovery |
|---|---|---|---|
| LipD (10 µl) + | 80 | 0.1 | 0.08 |
| LipD (10 µl) + 5 µl LimA | 80 | 44 | 35 |
| LipD (10 µl) + 10 µl LimA | 80 | 45 | 36 |
| LipD (10 µl) + 20 µl LimA | 80 | 56 | 45 |
| LipD (10 µl) + 30 µl LimA | 80 | 55 | 44 |
| LipD (10 µl) + 40 µl LimA | 80 | 53 | 42 |

Example 12

Constructions for LipD expression

The lipA sequence contains a MluI site at a position corresponding to 7 amino acids into the mature LipA sequence and a ClaI site following the lipA stop codon.

The lipD sequence contains MluI and ClaI sites at the equivalent positions.

Therefore, plasmids could easily be constructed based on the former lipA expression vectors by insertion of the lipD MluI-ClaI fragment in stead of the lipA MluI-ClaI fragment to allow expression of a hybrid protein, in which only the first 7 amino acids in the mature protein are from LipA, whereas the rest of the mature protein is from LipD.

pAHE16 (FIG. 11) expresses the LipA-LipD hybrid lipase together with LimA, and was constructed from pAHE2 by replacement of the MluI-ClaI fragment as described above. pAHE23 (FIG. 12) expresses only the LipA-LipD hybrid lipase, and no Lim protein. It was constructed from pAHE16 by deletion of the ClaI-NotI fragment of LimA.

Example 13

Denaturation/renaturation of the lipA-LipD hybrid lipase

The LipA-LipD hybrid protein expressed from pAHE16 and pAHE23 was used in a denaturation/renaturation experiment with and without LimA added as described in methods.

The lipase sample used in this experiment was the soluble fraction following lysis of the induced E. coli JA221 cells containing either pAHE16 or pAHE23 (although the vast majority of the lipase protein upon induction resides in inclusion bodies, the soluble fraction still contains some lipase, and there seem to be relatively more mature lipase in the soluble fraction than in the inclusion bodies).

LimA was obtained from an induced culture of BL21 (DE3) pLysS pCBE6.

The results presented below show that LimA is able to activate the LipA-LipD hybrid lipase in a denaturation/ renaturation experiment.

|  | LU before denaturation | LU after renaturation |
|---|---|---|
| pAHE16 (30 µl) + | 0.5 | 0.5 |
| pAHE16 (30 µl) + LimA (10 µl) | 0.5 | 0.75 |
| pAHE16 (30 µl) + LimA (20 µl) | 0.5 | 0.75 |
| pAHE16 (30 µl) + LimA (30 µl) | 0.5 | 0.75 |

-continued

|  | LU before denaturation | LU after renaturation |
|---|---|---|
| pAHE16 (30 µl) + LimA (40 µl) | 0.5 | 1.0 |
| pAHE16 (30 µl) + non-LimA cell lysate (40 µl) | 0.5 | 0.5 |
| pAHE23 (30 µl) + | 0.0 | 0.0 |
| pAHE23 (30 µl) + LimA (10 µl) | 0.0 | 0.75 |
| pAHE23 (30 µl) + LimA (20 µl) | 0.0 | 0.75 |
| pAHE23 (30 µl) + LimA (30 µl) | 0.0 | 1.0 |
| pAHE23 (30 µl) + LimA (40 µl) | 0.0 | 1.0 |
| pAHE23 (30 µl) + non-LimA cell lysate (40 µl) | 0.0 | 0.0 |

Example 14

Construction of lip-lim fusion

Plasmid pSJ721 is a deletion derivative of pSJ377 in which 15 bp have been deleted at the ClaI site, deleting the lipA stop codon, and the codons for the first three amino acids of lim (Jørgensen et al., J.Bacteriol., Vol. 173, pp. 559–67 (1991)). pSJ721 thus encodes a Lim protein which is fused to the eight amino acids following the SphI site at the C-terminal of lipA. The 838 bp SphI-NotI fragment of pSJ721 (which includes the C-terminal of lip fused to most of lim) and the 915 bp MluI-SphI fragment of pSJ150 (which includes most of the lipase coding sequence) were ligated with pAHE8 digested with MluI and NotI, such that a lip-lim fusion plasmid was generated. Transformants were screened for loss of the ClaI site which is normally present at the beginning of the limA gene and which is absent in pSJ721, and should be absent in lip-lim fusion plasmids. A number of plasmids were deemed to be correct from restriction enzyme analysis. Six of these were named pCBF1-6 (FIG. 13).

E. coli BL21(DE3) pLysS was transformed with each of the fusion plasmids and transformants were grown and induced with IPTG. Plating on tributyrine plates and analysis of activity in broth samples revealed that these plasmids gave rise to lipase activity upon induction. Protein samples from both cells and broth were analyzed on SDS-polyacrylamide gels and by western analysis using anti-lipase anti-serum. Only a lipase protein identical in size to the unprocessed lipase produced by pAHE2 or pAHE8 was detected. No proteins of the higher molecular weight expected were observed, even in samples taken early in time course induction experiments. Perhaps the artificial lip-lim fusion is particularly susceptible to proteolytic cleavage at the junction of the proteins.

In the Sequence Listing below

SEQ ID NO:1 is the nucleotide sequence of lipD;
SEQ ID NO:2 is the nucleotide sequence of limD;
SEQ ID NO:3 is the amino acid sequence of LipD. The sequence is that of the prelipase, the first amino acid residue of the mature lipase is A (amino acid residue 45).
SEQ ID NO:4 is the amino acid sequence of limD;
SEQ ID NO:5 is the nucleotide sequence of the lip-lim lip-lim fusion gene;
SEQ ID NO:6–8 are the peptide fragments discussed in Example 4; and
SEQ ID NO:9–11 are the nucleotide and amino acid sequences shown in Example 8.

What is claimed is:

1. A process for preparing an active Pseudomonas lipase enzyme which requires a chaperone for refolding in vitro, the process comprising (a) culturing a host cell transformed with a DNA sequence encoding a lipase enzyme under suitable conditions to produce the lipase enzyme in inactive or partly active form, recovering the lipase enzyme from the culture, and subjecting the recovered lipase enzyme to denaturation, (b) mixing the denatured lipase enzyme obtained in step (a) with a chaperone molecule, wherein the chaperone molecule is a Pseudomonas lipase modulator, and (c) subjecting the mixture of step (b) to renaturation, wherein said renaturation produces an active lipase enzyme.

2. The process of claim 1, wherein the chaperone molecule is produced by culturing a host cell transformed with a DNA sequence encoding the chaperone molecule under suitable conditions to produce the chaperone molecule and recovering the chaperone molecule from the culture.

3. The process of claim 1, wherein the chaperone molecule is subjected to a denaturation treatment before being added to the denatured lipase in step (b).

4. The process of claim 1, wherein the chaperone molecule is selected from the group consisting of *Pseudomonas cepacia* lipase modulator, the *Pseudomonas glumae* lipase modulator, the *Pseudomonas aeruginosa* lipase modulator.

5. A process of claim 1, wherein the lipase enzyme is a *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae*, or *Pseudomonas aeruginosa*.

6. The process of claim 5, wherein the lipase enzyme is a *Pseudomonas cepacia* lipase, and wherein the chaperone molecule is a *Pseudomonas cepacia* lipase modulator.

7. The process of claim 1, wherein the host cell for the production of the chaperone molecule is *E. coli*.

8. The process of claim 7, wherein the DNA sequence encoding the chaperone molecule is preceded by a promoter selected from the group consisting of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, or *Bacillus pumilus* xylosidase gene, or by the phage Lambda $P_R$ or $P_L$ promoters, the phage T7 gene 10 promoter or the *E. coli* lac promoter.

9. The process of claim 7, wherein the DNA sequence encoding the chaperone molecule is preceded by a ribosome binding site selected from the group consisting of the ribosome binding site of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, *Bacillus pumilus* xylosidase gene, phage T7 gene 10 or *E. coli* lac gene.

10. The process of claim 1, wherein the chaperone molecule is produced intracellularly in a yield of at least 5% of total cellular protein.

11. A process for preparing an active Pseudomonas lipase enzyme which requires a chaperone for refolding in vitro, the process comprising
  (a) culturing a host cell transformed with a DNA sequence encoding a lipase enzyme under suitable conditions to produce the lipase enzyme in inactive or partly active form and recovering the lipase enzyme from the culture,
  (b) mixing the recovered lipase enzyme with a chaperone molecule, wherein the chaperone molecule is a Pseudomonas lipase modulator, and
  (c) subjecting the mixture of step (b) to denaturation followed by renaturation, wherein said renaturation produces an active lipase enzyme.

12. The process of claim 11, wherein the chaperone molecule is produced by culturing a host cell transformed with a DNA sequence encoding the chaperone molecule under suitable conditions to produce the chaperone molecule and recovering the chaperone molecule from the culture.

13. The process of claim 1, wherein the chaperone molecule is subjected to a denaturation treatment before being added to the denatured lipase in step (b).

14. The process of claim 11, wherein the chaperone molecule is selected from the group consisting of *Pseudomonas cepacia* lipase modulator, the *Pseudomonas glumae* lipase modulator, the *Pseudomonas aeruginosa* lipase modulator.

15. A process of claim 11, wherein the lipase enzyme is a *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae*, or *Pseudomonas aeruginosa*.

16. The process of claim 15, wherein the lipase enzyme is a *Pseudomonas cepacia* lipase, and wherein the chaperone molecule is a *Pseudomonas cepacia* lipase modulator.

17. The process of claim 11, wherein the host cell for the production of the chaperone molecule is *E. coli*.

18. The process of claim 11, wherein the DNA sequence encoding the chaperone molecule is preceded by a promoter selected from the group consisting of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, or *Bacillus pumilus* xylosidase gene, or by the phage Lambda $P_R$ or $P_L$ promoters, the phage T7 gene 10 promoter or the *E. coli* lac promoter.

19. The process of claim 17, wherein the DNA sequence encoding the chaperone molecule is preceded by a ribosome binding site selected from the group consisting of the ribosome binding site of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, *Bacillus pumilus* xylosidase gene, phage T7 gene 10 or *E. coli* lac gene.

20. The process of claim 11, wherein the chaperone molecule is produced intracellularly in a yield of at least 5% of total cellular protein.

21. A process for preparing an active Pseudomonas lipase enzyme which requires a chaperone for refolding in vitro, the process comprising
  (a) culturing a host cell transformed with a DNA sequence encoding a lipase enzyme and with a DNA sequence encoding a chaperone molecule under suitable conditions to produce the lipase enzyme in inactive or partly active form and recovering a lipase enzyme chaperone molecule mixture from the culture, wherein the chaperone molecule is a Pseudomonas lipase modulator, and
  (b) subjecting the mixture of step (a) to denaturation followed by renaturation, wherein said renaturation produces an active lipase enzyme, optionally with addition of a further amount of chaperone molecule to the mixture.

22. The process of claim 21, wherein the chaperone molecule is selected from the group consisting of *Pseudomonas cepacia* lipase modulator, the *Pseudomonas glumae* lipase modulator, the *Pseudomonas aeruginosa* lipase modulator.

23. A process of claim 21, wherein the lipase enzyme is a *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae*, or *Pseudomonas aeruginosa*.

24. The process of claim 23, wherein the lipase enzyme is a *Pseudomonas cepacia* lipase, and wherein the chaperone molecule is a *Pseudomonas cepacia* lipase modulator.

25. The process of claim 24, wherein the host cell for the production of the chaperone molecule is *E. coli*.

26. The process of claim 25, wherein the DNA sequence encoding the chaperone molecule is preceded by a promoter selected from the group consisting of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, or *Bacillus pumilus* xylosidase gene, or by the phage Lambda $P_R$ or $P_L$ promoters, the phage T7 gene 10 promoter or the *E. coli* lac promoter.

27. The process of claim 25, wherein the DNA sequence encoding the chaperone molecule is preceded by a ribosome binding site selected from the group consisting of the ribosome binding site of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, *Bacillus pumilus* xylosidase gene, phage T7 gene 10 or *E. coli* lac gene.

28. The process of claim 21, wherein the chaperone molecule is produced intracellularly in a yield of at least 5% of total cellular protein.

29. A DNA construct comprising a first DNA sequence encoding a Pseudomonas lipase enzyme fused to a second DNA sequence encoding a Pseudomonas lipase modulator chaperone molecule, wherein the lipase enzyme and chaperone molecule are expressed as a single fusion protein on culturing a suitable host cell transformed with the DNA construct, and wherein the lipase enzyme is active.

30. The DNA construct of claim 29, wherein the first DNA sequence is one encoding a *Pseudomonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae,* or *Pseudomonas aeruginosa.*

31. The DNA construct of claim 29, wherein the second DNA sequence is one encoding a *Pseudomonas cepacia* lipase modulator, a *Pseudomonas glumae* lipase modulator, a *Pseudomonas aeroginosa* lipase modulator.

32. The DNA construct of claim 29, wherein the first DNA sequence encodes a *Pseudomonas cepacia* lipase and wherein the second DNA sequence encodes a *Pseudomonas cepacia* lipase modulator.

33. The DNA construct of claim 32, wherein the DNA construct has the DNA sequence of SEQ ID NO:5.

34. A recombinant expression vector comprising the DNA construct of claim 29.

35. A host cell transformed with the vector of claim 34.

36. The host cell of claim 35, wherein the cell is a strain of *E. coli.*

37. The host cell of claim 36, wherein the DNA construct is preceded by the promoter of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, or *Bacillus pumilus* xylosidase gene, or by the phage Lambda $P_R$ or $P_L$ promoters, the phage T7 gene 10 promoter or the *E. coli* lac promoter.

38. The host cell of claim 36, wherein the DNA construct is preceded by the ribosome binding site of the *Bacillus stearothermophilus* maltogenic amylase gene, *Bacillus licheniformis* α-amylase gene, *Bacillus amyloliquefaciens* α-amylase gene, *Bacillus subtilis* alkaline protease gene, *Bacillus pumilus* xylosidase gene, phage T7 gene 10 or *E. coli* lac gene.

39. A process for preparing a lipase in active form, the process comprising culturing the host cell of claim 35 under suitable conditions to produce the lipase, and recovering the lipase from the culture.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1092 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Pseudomonas cepacia
        ( B ) STRAIN: DSM 3401

( x i ) SEQUENCE DESCRIPTION: SEQ ID NO:1:

```
ATGGCCAGAT CGATGCGTTC CAGGGTGGTG GCAGGGGCAG TGGCATGCGC GATGAGCGTC        60
GCGCCGTTCG CGGGGGCGAC CGCGGTGATG ACGCTTGCGA CGACGCACGC GGCGATGGCG       120
GCGACCGCGC CCGCCGACGA CTACGCGACG ACGCGTTATC CGATCATCCT CGTGCACGGG       180
CTCACGGGTA CCGACAAGTA CGCGGGCGTG CTCGAGTACT GGTACGGCAT CCAGGAAGAC       240
CTGCAGCAGC ATGGCGCGAC CGTCTACGTC GCGAACCTGT CGGGCTTCCA GAGCGACGAC       300
GGGCCGAACG GCGCGGCGA ACAGTTGCTC GCGTACGTGA AGACGGTGCT CGCGGCGACG        360
GGCGCGACCA AGGTCAATCT CGTCGGCCAC NGCAGGGCG GGCTCACGTC GCGTTACGTT        420
GCGGCTGTCG CGCCCGATCT CGTCGCGTCG GTGACGACGA TCGGCACGCC GCATCGTGCN       480
NCCGAGTTCG CCGACTTCGT GCAGGGCGTG CTCGCATACG ATCCGACCGG GCTTTCGTCA       540
TCGGTGATCG CGGCGTTCGT CAATGTGTTC GGAATCCTGA CGAGCAGCAG CCACAACACG       600
AACCAGGACG CACTCGCGTC GCTGAAGACG CTGACGACCG CCCAGGCCGC CGCGTACAAC       660
CAGAACTATC CGAGCGCGGG CCTCGGTGCG CCGGGCAGTT GCCAGACCGG CNNNCCGACG       720
GAAACCGTGC GGTNCAACAC GCATCTGCTG TATTCGTGGG CCGGCACGGC GATCCAGCCG       780
ACGCTCTCCG TGTTCGGTGT CACGGGCGCG ACGGACACGA GCACCATTCC GCTCGTCGAT       840
CCGGCGAACG CGCTCGACCC GTCGACGCTT GCGCTGTTCG GCACGGGCAC GGTGATGATC       900
AACCGCGGCT CGGGCCCGAA CGACGGGCTC GTATCGAAGT GCAGCGCGCT GTACGGCCAG       960
GTGCTGAGCA CGAGCTACAA GTGGAACCAT ATCGACGAGA TCAACCAGTT GCTCGGCGTG      1020
CGCGGCGCGA ATGCGGAAGA TCCCGTCGCG GTGATCCGCA CGCATGCGAA CCGGCTGAAG      1080
CTGGCGGGCG TG                                                          1092
```

( 2 ) INFORMATION FOR SEQ ID NO:2:

( i ) SEQUENCE CHARACTERISTICS:
        ( A ) LENGTH: 1032 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v ) FRAGMENT TYPE: internal ( v i ) ORIGINAL SOURCE:
    ( A ) ORGANISM: Pseudomonas cepacia
    ( B ) STRAIN: DSM 3401

( x i ) SEQUENCE DESCRIPTION: SEQ ID NO:2:

```
ATGGCGGCAC GTGAAGGGCG CGCGCCGCTG GCGCGGCGCG CTGCAGTCTA CGGTGTCGTG      60
GGGCTGGCGG CGATCGCCGG CGTCGCGATG TGGAGCGGGG CGGGATGGCA TCGCGGTACG     120
GGTAGCGTCG GCGAAGCGCC CGATGCGGCG GCAGTGGGCG GCGTGGCTGC GGCACCGCCG     180
CAGGCGGCCG TGCCGGCGAG CGCGGGCCTG CCGTCGTCGC TGGCCGGCTC CAGCGCGCCG     240
CGCGTGCCGC TCGATGCGGG CGGCCATCTC GCGAAGGTGC GCGCGGTGCG CGATTTCTTC     300
GACTACTGCC TGACCGCGCA GAGCGACCTC AGTGCGGCCG CGCTCGATGC ACTCGTCGTG     360
CGCGAGATTG CCGCGCAGCT CGACGGCACG GCGGCGCAGG CCGAGGCGCT CGACGTGTGG     420
CATCGCTATC GTGCGTATCT CGACGCGCTC GCGAAACTGC GCGATGCCGG CGCGGTCGAC     480
AAGTCCGACC TGGGCGCGCT GCAGCTCGCG CTCGACCAGC GCGCATCGAT CGCGTATCGC     540
ACGCTCGGCG ACTGGAGCCA GCCGTTCTTC GGCGCGGAGC AGTGGCGGCA GCGCTACGAT     600
CTCGCGCGGC TGAAGATCGC GCAGGATCGC ACGCTGACCG ATGCGCAGAA GGCCGAACGG     660
CTCGCGGCGC TGCAGCAACA GATGCCGGCC GACGAACGCG CGGCTCAGCA GGCGGTCGAC     720
CGGCAGCGGG CCGCGATCGA CCAGAGTCCG NAGTTGCAGA AGAGCGGGAC GACGCCCGAT     780
GCGATGCGCG CGCAACTGAC GCAGACGCTC GGGCCCGAGG CCGCCGCGCG CGTCGGCCAG     840
ATGCAGCAGG ACGACGCATC GTGGCAGAGN CGCTACGCGG ACTATGCGGC GCAGCGCGCG     900
CAGATCGAGT CGGCCGGCCT GTCGCCGCAG GGCCGCGACG CGCAGATCGC CGCACTGCGG     960
CAGCGCGTGT TCACGAAGCC CGGCGAAGCC GTGCGCGCGG CGTCGCTCGA TCGCGGGGCG    1020
GGCAGCGCGC AG                                                       1032
```

( 2 ) INFORMATION FOR SEQ ID NO:3:

( i ) SEQUENCE CHARACTERISTICS:
        ( A ) LENGTH: 364 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Pseudomonas cepacia
        ( B ) STRAIN: DSM 3401

( x i ) SEQUENCE DESCRIPTION: SEQ ID NO:3:

```
Met Ala Arg Ser Met Arg Ser Arg Val Val Ala Gly Ala Val Ala Cys
 1               5                  10                  15

Ala Met Ser Val Ala Pro Phe Ala Gly Ala Thr Ala Val Met Thr Leu
                20                  25                  30

Ala Thr Thr His Ala Ala Met Ala Ala Thr Ala Pro Ala Asp Asp Tyr
                35                  40                  45

Ala Thr Thr Arg Tyr Pro Ile Ile Leu Val His Gly Leu Thr Gly Thr
```

```
              50                          55                          60
    Asp  Lys  Tyr  Ala  Gly  Val  Leu  Glu  Tyr  Trp  Tyr  Gly  Ile  Gln  Glu  Asp
    65                       70                      75                       80

Leu  Gln  Gln  His  Gly  Ala  Thr  Val  Tyr  Val  Ala  Asn  Leu  Ser  Gly  Phe
                        85                      90                      95

Gln  Ser  Asp  Asp  Gly  Pro  Asn  Gly  Arg  Gly  Glu  Gln  Leu  Leu  Ala  Tyr
                   100                      105                     110

Val  Lys  Thr  Val  Leu  Ala  Ala  Thr  Gly  Ala  Thr  Lys  Val  Asn  Leu  Val
              115                     120                     125

Gly  His  Xaa  Gln  Gly  Gly  Leu  Thr  Ser  Arg  Tyr  Val  Ala  Ala  Val  Ala
         130                     135                     140

Pro  Asp  Leu  Val  Ala  Ser  Val  Thr  Thr  Ile  Gly  Thr  Pro  His  Arg  Xaa
    145                     150                     155                          160

Xaa  Glu  Phe  Ala  Asp  Phe  Val  Gln  Gly  Val  Leu  Ala  Tyr  Asp  Pro  Thr
                        165                     170                     175

Gly  Leu  Ser  Ser  Ser  Val  Ile  Ala  Ala  Phe  Val  Asn  Val  Phe  Gly  Ile
                   180                     185                     190

Leu  Thr  Ser  Ser  Ser  His  Asn  Thr  Asn  Gln  Asp  Ala  Leu  Ala  Ser  Leu
              195                     200                     205

Lys  Thr  Leu  Thr  Thr  Ala  Gln  Ala  Ala  Ala  Tyr  Asn  Gln  Asn  Tyr  Pro
         210                     215                     220

Ser  Ala  Gly  Leu  Gly  Ala  Pro  Gly  Ser  Cys  Gln  Thr  Gly  Xaa  Pro  Thr
    225                     230                     235                          240

Glu  Thr  Val  Arg  Xaa  Asn  Thr  His  Leu  Leu  Tyr  Ser  Trp  Ala  Gly  Thr
                        245                     250                     255

Ala  Ile  Gln  Pro  Thr  Leu  Ser  Val  Phe  Gly  Val  Thr  Gly  Ala  Thr  Asp
                   260                     265                     270

Thr  Ser  Thr  Ile  Pro  Leu  Val  Asp  Pro  Ala  Asn  Ala  Leu  Asp  Pro  Ser
              275                     280                     285

Thr  Leu  Ala  Leu  Phe  Gly  Thr  Gly  Thr  Val  Met  Ile  Asn  Arg  Gly  Ser
         290                     295                     300

Gly  Pro  Asn  Asp  Gly  Leu  Val  Ser  Lys  Cys  Ser  Ala  Leu  Tyr  Gly  Gln
    305                     310                     315                          320

Val  Leu  Ser  Thr  Ser  Tyr  Lys  Trp  Asn  His  Ile  Asp  Glu  Ile  Asn  Gln
                        325                     330                     335

Leu  Leu  Gly  Val  Arg  Gly  Ala  Asn  Ala  Glu  Asp  Pro  Val  Ala  Val  Ile
                   340                     345                     350

Arg  Thr  His  Ala  Asn  Arg  Leu  Lys  Leu  Ala  Gly  Val
              355                     360
```

( 2 ) INFORMATION FOR SEQ ID NO:4:

( i ) SEQUENCE CHARACTERISTICS:
        ( A ) LENGTH: 344 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Pseudomonas cepacia
        ( B ) STRAIN: DSM 3401

( x i ) SEQUENCE DESCRIPTION: SEQ ID NO:4:

| Met | Ala | Ala | Arg | Glu | Gly | Arg | Ala | Pro | Leu | Ala | Arg | Arg | Ala | Ala | Val |
|---|---|---|---|---|---|---|---|---|---|---|---|---|---|---|---|
| 1 | | | | 5 | | | | | 10 | | | | | 15 | |
| Tyr | Gly | Val | Val | Gly | Leu | Ala | Ala | Ile | Ala | Gly | Val | Ala | Met | Trp | Ser |
| | | | 20 | | | | | 25 | | | | | 30 | | |
| Gly | Ala | Gly | Trp | His | Arg | Gly | Thr | Gly | Ser | Val | Gly | Glu | Ala | Pro | Asp |
| | | 35 | | | | | 40 | | | | | 45 | | | |
| Ala | Ala | Ala | Val | Gly | Gly | Val | Ala | Ala | Pro | Pro | Gln | Ala | Ala | Val | |
| | 50 | | | | | 55 | | | | 60 | | | | | |
| Pro | Ala | Ser | Ala | Gly | Leu | Pro | Ser | Ser | Leu | Ala | Gly | Ser | Ser | Ala | Pro |
| 65 | | | | | 70 | | | | 75 | | | | | | 80 |
| Arg | Val | Pro | Leu | Asp | Ala | Gly | Gly | His | Leu | Ala | Lys | Val | Arg | Ala | Val |
| | | | | 85 | | | | | 90 | | | | | 95 | |
| Arg | Asp | Phe | Phe | Asp | Tyr | Cys | Leu | Thr | Ala | Gln | Ser | Asp | Leu | Ser | Ala |
| | | | 100 | | | | | 105 | | | | | 110 | | |
| Ala | Ala | Leu | Asp | Ala | Leu | Val | Val | Arg | Glu | Ile | Ala | Ala | Gln | Leu | Asp |
| | | | 115 | | | | 120 | | | | | 125 | | | |
| Gly | Thr | Ala | Ala | Gln | Ala | Glu | Ala | Leu | Asp | Val | Trp | His | Arg | Tyr | Arg |
| | 130 | | | | | 135 | | | | | 140 | | | | |
| Ala | Tyr | Leu | Asp | Ala | Leu | Ala | Lys | Leu | Arg | Asp | Ala | Gly | Ala | Val | Asp |
| 145 | | | | | 150 | | | | | 155 | | | | | 160 |
| Lys | Ser | Asp | Leu | Gly | Ala | Leu | Gln | Leu | Ala | Leu | Asp | Gln | Arg | Ala | Ser |
| | | | | 165 | | | | | 170 | | | | | 175 | |
| Ile | Ala | Tyr | Arg | Thr | Leu | Gly | Asp | Trp | Ser | Gln | Pro | Phe | Phe | Gly | Ala |
| | | | 180 | | | | | 185 | | | | | 190 | | |
| Glu | Gln | Trp | Arg | Gln | Arg | Tyr | Asp | Leu | Ala | Arg | Leu | Lys | Ile | Ala | Gln |
| | | 195 | | | | | 200 | | | | | 205 | | | |
| Asp | Arg | Thr | Leu | Thr | Asp | Ala | Gln | Lys | Ala | Glu | Arg | Leu | Ala | Ala | Leu |
| | 210 | | | | | 215 | | | | | 220 | | | | |
| Gln | Gln | Gln | Met | Pro | Ala | Asp | Glu | Arg | Ala | Ala | Gln | Gln | Ala | Val | Asp |
| 225 | | | | | 230 | | | | | 235 | | | | | 240 |
| Arg | Gln | Arg | Ala | Ala | Ile | Asp | Gln | Ser | Pro | Xaa | Leu | Gln | Lys | Ser | Gly |
| | | | | 245 | | | | | 250 | | | | | 255 | |
| Thr | Thr | Pro | Asp | Ala | Met | Arg | Ala | Gln | Leu | Thr | Gln | Thr | Leu | Gly | Pro |
| | | | 260 | | | | | 265 | | | | | 270 | | |
| Glu | Ala | Ala | Ala | Arg | Val | Gly | Gln | Met | Gln | Gln | Asp | Asp | Ala | Ser | Trp |
| | | 275 | | | | | 280 | | | | | 285 | | | |
| Gln | Xaa | Arg | Tyr | Ala | Asp | Tyr | Ala | Ala | Gln | Arg | Ala | Gln | Ile | Glu | Ser |
| | 290 | | | | | 295 | | | | | 300 | | | | |
| Ala | Gly | Leu | Ser | Pro | Gln | Gly | Arg | Asp | Ala | Gln | Ile | Ala | Ala | Leu | Arg |
| 305 | | | | | 310 | | | | | 315 | | | | | 320 |
| Gln | Arg | Val | Phe | Thr | Lys | Pro | Gly | Glu | Ala | Val | Arg | Ala | Ala | Ser | Leu |
| | | | | 325 | | | | | 330 | | | | | 335 | |
| Asp | Arg | Gly | Ala | Gly | Ser | Ala | Gln | | | | | | | | |
| | | | 340 | | | | | | | | | | | | |

( 2 ) INFORMATION FOR SEQ ID NO:5:

( i ) SEQUENCE CHARACTERISTICS:
( A ) LENGTH: 2118 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v ) FRAGMENT TYPE: internal ( x i ) SEQUENCE DESCRIPTION: SEQ ID NO:5:

```
ATGGCCAGGA CGATGCGTTC CAGGGTGGTG GCAGGGGCAG TGGCATGCGC GATGAGCATC      60
GCGCCGTTCG CGGGGACGAC CGCGGTGATG ACGCTCGCGA CGACGCACGC GGCAATGGCG     120
GCCACCGCGC CCGCCGCTGG CTACGCGGCG ACGCGTTACC CGATCATCCT CGTGCACGGG     180
CTCTCGGGTA CCGACAAGTA CGCCGGCGTG CTCGAGTATT GGTACGGCAT CCAGGAGGAC     240
CTGCAACAGA ACGGTGCGAC CGTCTACGTC GCGAACCTGT CGGGTTTCCA GAGCGACGAC     300
GGCCCGAACG GGCGCGGCGA ACAGTTGCTC GCTTACGTGA AGACGGTGCT CGCGGCGACG     360
GGGGCGACCA AGGTCAATCT CGTCGGTCAC AGCCAGGGCG GCCTCTCGTC GCGCTATGTT     420
GCTGCCGTCG CGCCCGATCT CGTTGCGTCG GTGACGACGA TCGGCCCAGC CGATCGCGGC     480
TCCGAATTCG CCGACTTCGT GCAGGACGTG CTCGCGTACG ATCCGACCGG GCTTTCGTCA     540
TCGGTGATCG CCGCGTTCGT CAATGTGTTC GGGATCCTGA CGAGCAGCAG CCACAACACC     600
AACCAGGACG CGCTCGCCGC ACTGCAGACG CTGACCACCG CACGGGCCGC CACGTACAAC     660
CAGAACTATC CGAGCGCGGG CCTGGGTGCG CCGGGCAGTT GCCAGACCGG TGCGCCGACC     720
GAAACCGTCG GCGGCAACAC GCACCTGCTG TATTCGTGGG CCGGCACGGC GATCCAGCCG     780
ACGCTCTCCG TGTTCGGCGT CACGGGCGCG ACGGACACGA GCACCCTTCC GCTCGTCGAT     840
CCGGCGAACG TGCTCGACCT GTCGACGCTC GCGCTGTTCG GCACCGGCAC GGTGATGATC     900
AACCGCGGCT CCGGGCAGAA CGACGGGCTC GTGTCGAAGT GCAGTGCGCT GTACGGCAAG     960
GTGCTGAGCA CGAGCTACAA GTGGAACCAC CTCGACGAGA TCAACCAGCT GCTCGGCGTG    1020
CGCGGCGCGT ATGCGGAAGA TCCCGTCGCG GTGATCCGCA CGCATGCGAA CCGGCTGAAG    1080
CTGGCGGGGG CACGAGGAGG ACGCGCGCCG CTGGCGCGCC GCGCCGTGGT CTATGGTGCC    1140
GTGGGGCTGG CGGCGATTGC CGGCGTGGCG ATGTGGAGCG GCGCGGGCCG GCATGGCGGG    1200
ACGGGCGCAT CCGGCGAGCC GCCGGATGCG TCGGCGGCAC GCGGACCGGC TGCCGCACCG    1260
CCGCAGGCCG CCGTGCCGGC AAGCACGAGC CTGCCGCCGT CGCTCGCCGG CTCCAGCGCG    1320
CCCCGCTTGC CGCTCGATGC CGGCGGCCAT CTCGCGAAGG CGCGCGCGGT GCGGGATTTC    1380
TTCGACTACT GCCTGACCGC GCAGAGCGAC CTGAGTGCGG CCGGGCTCGA TGCGTTCGTC    1440
ATGCGCGAGA TTGCCGCACA GCTCGACGGG ACCGTTGCGC AGGCCGAGGC GCTCGACGTG    1500
TGGCACCGGT ATCGCGCGTA TCTCGACGCA CTCGCGAAAT GCGCGATGC CGGCGCGGTC     1560
GACAAGTCGG ACCTGGGTGC ATTGCAGCTC GCGCTCGACC AGCGCGCGTC GATCGCGTAC    1620
CGGTGGCTCG GCGACTGGAG CCAGCCGTTC TTCGGTGCGG AGCAATGGCG GCAGCGCTAC    1680
GACCTCGCGC GGCTGAAGAT CGCGCAGGAC CCCGCGCTGA CGGATGCGCA GAAGGCCGAA    1740
CGGCTCGCGG CGCTCGAACA GCAGATGCCG GCCGACGAAC GCGCCGCGCA GCAGCGCGTC    1800
GACCGGCAGC GCGCGGCGAT CGACCAGATC GCGCAATTGC AGAAGAGCGG GGCGACGCCC    1860
GATGCGATGC GCGCACAACT GACGCAGACG CTCGGCCCCG AAGCGGCCGC GCGCGTCGCG    1920
CAGATGCAGC AGGACGACGC ATCGTGGCAG AGGCGCTACG CGGACTACGC GGCGCAGCGT    1980
GCGCAGATCG AGTCGGCCGG CCTGTCGCCG CAGGATCGCG ACGCGCAGAT CGCCGCGCTG    2040
CGGCAGCGCG TGTTTACGAA GCCCGGCGAA GCCGTGCGCG CGGCATCGCT CGATCGCGGG    2100
GCGGGCAGCG CGCGGTAA                                                  2118
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Pseudomonas cepacia
        ( B ) STRAIN: DSM3959

( x i ) SEQUENCE DESCRIPTION: SEQ ID NO:6:

```
Thr Ala Arg Gly Gly Arg Ala Pro Leu Arg Arg Ala Val Val Tyr Gly
1               5                   10                  15
Ala Val Gly
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Pseudomonas cepacia
        ( B ) STRAIN: DSM3959

( x i ) SEQUENCE DESCRIPTION: SEQ ID NO:7:

```
Ala Arg Thr Met Arg Ser Arg Val Val Ala Gly Ala Val Ala Ala Met
1               5                   10                  15
Ser Ile Ala
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( v i ) ORIGINAL SOURCE:
        ( A ) ORGANISM: Pseudomonas cepacia
        ( B ) STRAIN: DSM3959

( x i ) SEQUENCE DESCRIPTION: SEQ ID NO:8:

```
Ala Arg Thr Met Arg Ser Arg Val Val Ala Gly Ala Val Ala Met Ile
1               5                   10                  15
```

Ala (2) INFORMATION FOR SEQ ID NO:9:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (v) FRAGMENT TYPE: internal (xi) SEQUENCE DESCRIPTION: SEQ ID NO:9:

```
CGCGTAAGCT TCACATTGAA AGGGGAGGAG AATCATGGCC GCTGGCTACG CGGCGA         56
```

(2) INFORMATION FOR SEQ ID NO:10:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (v) FRAGMENT TYPE: internal (xi) SEQUENCE DESCRIPTION: SEQ ID NO:10:

```
CGCGTCGCCG CGTAGCCAGC GGCCATGATT CTCCTCCCCT TTCAATGTGA AGCTTA         56
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: N-terminal (vi) ORIGINAL SOURCE:
        (A) ORGANISM: Pseudomonas cepacia
        (B) STRAIN: DSM3959

(xi) SEQUENCE DESCRIPTION: SEQ ID NO:11:

Ala Ala Gly Tyr Ala Ala
1             5